(12) United States Patent
Kang et al.

(10) Patent No.: US 11,136,394 B2
(45) Date of Patent: Oct. 5, 2021

(54) ANTIBODY BINDING PD-1 AND USE THEREOF

(71) Applicant: Nanjing Leads Biolabs Co. Ltd., Nanjing (CN)

(72) Inventors: Xiaoqiang Kang, Plainshoro, NJ (US); Shoupeng Lai, Germantown, MD (US); Xiao Huang, Nanjing (CN)

(73) Assignee: Nanjing Leads Biolabs Co., Ltd., Nanjing (CN)

( * ) Notice: Subject to any disclaimer, the term of this patent is extended or adjusted under 35 U.S.C. 154(b) by 223 days.

(21) Appl. No.: 16/414,724

(22) Filed: May 16, 2019

(65) Prior Publication Data
US 2019/0352402 A1    Nov. 21, 2019

Related U.S. Application Data

(60) Provisional application No. 62/672,602, filed on May 17, 2018.

(51) Int. Cl.
| | | |
|---|---|---|
| A61K 39/00 | (2006.01) | |
| C07K 16/28 | (2006.01) | |
| C07K 14/55 | (2006.01) | |
| A61P 35/00 | (2006.01) | |
| A61K 9/00 | (2006.01) | |
| A61K 45/06 | (2006.01) | |

(52) U.S. Cl.
CPC ........ *C07K 16/2827* (2013.01); *A61K 9/0019* (2013.01); *A61P 35/00* (2018.01); *C07K 14/55* (2013.01); *C07K 16/2818* (2013.01); *C07K 16/2878* (2013.01); *C07K 16/2896* (2013.01); *A61K 45/06* (2013.01); *A61K 2039/505* (2013.01)

(58) Field of Classification Search
CPC ............................................... A61K 2039/505
See application file for complete search history.

(56) References Cited

U.S. PATENT DOCUMENTS

| 9,217,034 B2 | 12/2015 | Li et al. |
|---|---|---|
| 2017/0044260 A1 | 2/2017 | Baruah et al. |

FOREIGN PATENT DOCUMENTS

| CN | 101213297 B | 2/2013 |
|---|---|---|
| WO | WO 2006/121168 A1 | 11/2006 |
| WO | WO 2014/206107 A1 | 12/2014 |
| WO | WO 2015/085847 A1 | 6/2015 |
| WO | WO 2015/112800 A1 | 7/2015 |
| WO | WO 2016/077397 A2 | 5/2016 |
| WO | WO 2017/087589 A2 | 5/2017 |

OTHER PUBLICATIONS

Topalian et al., Safety, activity, and immune correlates of anti-PD-1 antibody in cancer. N Engl J Med. Jun. 28, 2012;366(26):2443-54. doi: 10.1056/NEJMoa1200690. Epub Jun. 2, 2012.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

*Primary Examiner* — Stephen L Rawlings
(74) *Attorney, Agent, or Firm* — Wolf, Greenfield & Sacks, P.C.

(57) ABSTRACT

The present invention provides an isolated monoclonal antibody that specifically binds human PD-1. A nucleic acid molecule encoding the antibody, an expression vector, a host cell and a method for expressing the antibody are also provided. The present invention further provides an immunoconjugate, a bispecific molecule and a pharmaceutical composition comprising the antibody, as well as a diagnostic and treatment method using an anti-PD-1 antibody of the invention.

24 Claims, 6 Drawing Sheets

Specification includes a Sequence Listing.

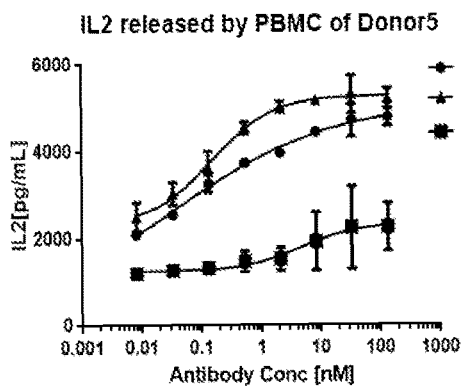 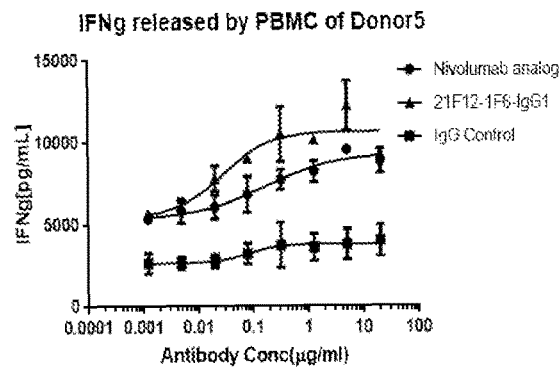
FIG. 8A  FIG. 8B
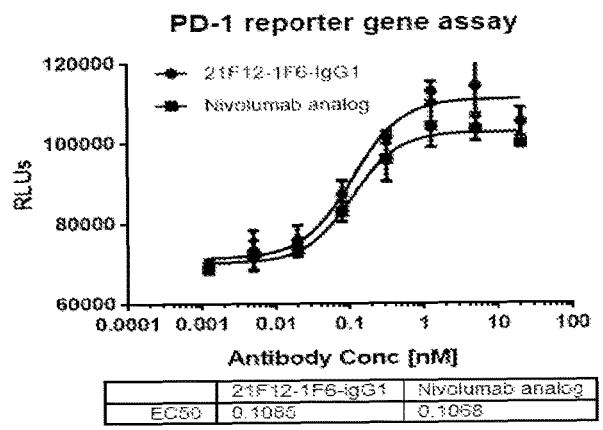
FIG. 9
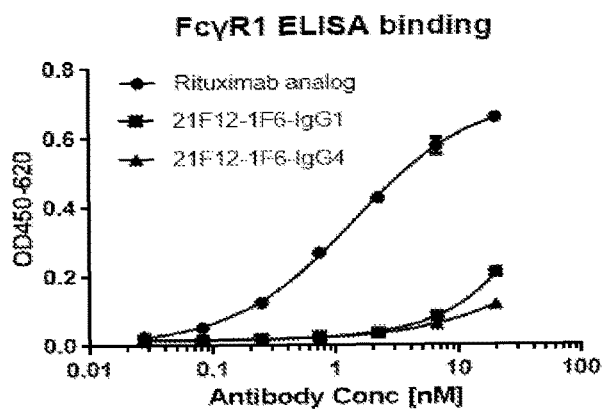
FIG. 10

SEQUENCE LISTING

<160> NUMBER OF SEQ ID NOS: 71

<210> SEQ ID NO 1
<211> LENGTH: 5
<212> TYPE: PRT
<213> ORGANISM: Artificial Sequence
<220> FEATURE:
<223> OTHER INFORMATION: VH-CDR1 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 1

Ser Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: VH-CDR2 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 2

Val Ile Asn Pro Ser Gly Gly Ser Thr Thr Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: VH-CDR3 for 21F12, 21F12-1B12, 21F12-1E11,
      21F12-2E1, 21F12-2H7, 21F12-1C4, 21F12-1E10, 21F12-1F6

<400> SEQUENCE: 3

Gly Ser Tyr Ser Ser Gly Trp Asp Tyr Tyr Tyr Tyr Gly Met Asp
1               5                   10                  15

Val

<210> SEQ ID NO 4
<211> LENGTH: 17
<212> TYPE: PRT
<213> ORGANISM: Artificial Sequence
<220> FEATURE:
<223> OTHER INFORMATION: VH-CDR3 for 21F12-3G1

<400> SEQUENCE: 4

Gly Ser Tyr Asn Ser Gly Trp Asp Tyr Tyr Tyr Tyr Gly Met Asp
1               5                   10                  15

Val

<210> SEQ ID NO 5
<211> LENGTH: 16
<212> TYPE: PRT
<213> ORGANISM: Artificial Sequence
<220> FEATURE:
<223> OTHER INFORMATION: VL-CDR1 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 5

Arg Ser Ser Gln Ser Leu Leu His Ser Gln Gly Tyr Asn Tyr Leu Asp
1               5                   10                  15

```
<210> SEQ ID NO 6
<211> LENGTH: 7
<212> TYPE: PRT
<213> ORGANISM: Artificial Sequence
<220> FEATURE:
<223> OTHER INFORMATION: VL-CDR2 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 6

Leu Gly Ser Asn Arg Ala Ser
1               5

<210> SEQ ID NO 7
<211> LENGTH: 9
<212> TYPE: PRT
<213> ORGANISM: Artificial Sequence
<220> FEATURE:
<223> OTHER INFORMATION: VL-CDR3 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 7

Met Gln Ala Leu Gln Thr Pro Trp Thr
1               5

<210> SEQ ID NO 8
<211> LENGTH: 126
<212> TYPE: PRT
<213> ORGANISM: Artificial Sequence
<220> FEATURE:
<223> OTHER INFORMATION: VH for 21F12

<400> SEQUENCE: 8

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser
        115                 120                 125

<210> SEQ ID NO 9
<211> LENGTH: 126
<212> TYPE: PRT
<213> ORGANISM: Artificial Sequence
<220> FEATURE:
<223> OTHER INFORMATION: VH for 21F12-1B12

<400> SEQUENCE: 9

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
```

```
                    20                  25                  30
Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser
        115                 120                 125

<210> SEQ ID NO 10
<211> LENGTH: 126
<212> TYPE: PRT
<213> ORGANISM: Artificial Sequence
<220> FEATURE:
<223> OTHER INFORMATION: VH for 21F12-1E11

<400> SEQUENCE: 10

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Phe Phe Gln Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser
        115                 120                 125

<210> SEQ ID NO 11
<211> LENGTH: 126
<212> TYPE: PRT
<213> ORGANISM: Artificial Sequence
<220> FEATURE:
<223> OTHER INFORMATION: VH for 21F12-2E1

<400> SEQUENCE: 11

Gln Met Gln Leu Val Gln Ser Gly Ala Glu Val Lys Lys Pro Gly Ala
1               5                   10                  15

Ser Val Lys Leu Ser Cys Lys Ala Ser Glu Tyr Ile Phe Gln Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Val Val Tyr Tyr Cys
            85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser
            115                 120                 125

<210> SEQ ID NO 12
<211> LENGTH: 126
<212> TYPE: PRT
<213> ORGANISM: Artificial Sequence
<220> FEATURE:
<223> OTHER INFORMATION: VH for 21F12-2H7

<400> SEQUENCE: 12

Gln Met Gln Leu Val Gln Ser Gly Ala Glu Val Lys Lys Pro Gly Ala
1               5                   10                  15

Ser Val Lys Leu Ser Cys Lys Ala Ser Gln Tyr Ile Phe Gln Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
            85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser
            115                 120                 125

<210> SEQ ID NO 13
<211> LENGTH: 126
<212> TYPE: PRT
<213> ORGANISM: Artificial Sequence
<220> FEATURE:
<223> OTHER INFORMATION: VH for 21F12-1C4

<400> SEQUENCE: 13

Gln Met Gln Leu Val Gln Ser Gly Ala Glu Val Lys Lys Pro Gly Ala
1               5                   10                  15

Ser Val Lys Leu Ser Cys Lys Ala Ser Asp Tyr Ile Phe Thr Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
            85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser
            115                 120                 125

<210> SEQ ID NO 14
```

```
<211> LENGTH: 126
<212> TYPE: PRT
<213> ORGANISM: Artificial Sequence
<220> FEATURE:
<223> OTHER INFORMATION: VH for 21F12-1E10

<400> SEQUENCE: 14

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser
        115                 120                 125

<210> SEQ ID NO 15
<211> LENGTH: 126
<212> TYPE: PRT
<213> ORGANISM: Artificial Sequence
<220> FEATURE:
<223> OTHER INFORMATION: VH for 21F12-1F6

<400> SEQUENCE: 15

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser
        115                 120                 125

<210> SEQ ID NO 16
<211> LENGTH: 126
<212> TYPE: PRT
<213> ORGANISM: Artificial Sequence
<220> FEATURE:
<223> OTHER INFORMATION: VH for 21F12-3G1

<400> SEQUENCE: 16

Gln Met Gln Leu Val Gln Ser Gly Ala Glu Val Lys Lys Pro Gly Ala
1               5                   10                  15
```

Ser Val Lys Leu Ser Cys Lys Ala Ser Gly Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Asn Ser Gly Trp Asp Tyr Tyr Tyr Tyr Gly
            100                 105                 110

Met Asp Val Trp Gly Lys Gly Thr Leu Val Thr Val Ser Ser
        115                 120                 125

<210> SEQ ID NO 17
<211> LENGTH: 112
<212> TYPE: PRT
<213> ORGANISM: Artificial Sequence
<220> FEATURE:
<223> OTHER INFORMATION: VL for 21F12, 21F12-1B12, 21F12-1E11, 21F12-
      2E1, 21F12-2H7, 21F12-1C4, 21F12-1E10, 21F12-1F6, and 21F12-3G1

<400> SEQUENCE: 17

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Gln Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 18
<211> LENGTH: 330
<212> TYPE: PRT
<213> ORGANISM: Artificial Sequence
<220> FEATURE:
<223> OTHER INFORMATION: mutant IgG1 CH for 21F12, 21F12-1B12, 21F12-
      1E11, 21F12-2E1, 21F12-2H7, 21F12-1C4, 21F12-1E10, 21F12-1F6, and
      21F12-3G1

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 327
<212> TYPE: PRT
<213> ORGANISM: Artificial Sequence
<220> FEATURE:
<223> OTHER INFORMATION: IgG4 CH for 21F12, 21F12-1B12, 21F12-1E11,
    21F12-2E1, 21F12-2H7, 21F12-1C4, 21F12-1E10, 21F12-1F6, and
    21F12-3G1

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

```
Arg Val Glu Ser Lys Tyr Gly Pro Pro Cys Pro Cys Pro Ala Pro
                100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 20
<211> LENGTH: 107
<212> TYPE: PRT
<213> ORGANISM: Artificial Sequence
<220> FEATURE:
<223> OTHER INFORMATION: CL for 21F12, 21F12-1B12, 21F12-1E11, 21F12-
      2E1, 21F12-2H7, 21F12-1C4, 21F12-1E10, 21F12-1F6, and 21F12-3G1

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 21
```

<211> LENGTH: 456
<212> TYPE: PRT
<213> ORGANISM: Artificial Sequence
<220> FEATURE:
<223> OTHER INFORMATION: Heavy chain for 21F12

<400> SEQUENCE: 21

```
Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380
```

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
    435                 440                 445

Ser Leu Ser Leu Ser Pro Gly Lys
450                 455

<210> SEQ ID NO 22
<211> LENGTH: 453
<212> TYPE: PRT
<213> ORGANISM: Artificial Sequence
<220> FEATURE:
<223> OTHER INFORMATION: Heavy chain for 21F12

<400> SEQUENCE: 22

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285
```

Glu Val His Asn Ala Lys Thr Lys Pro Arg Glu Glu Gln Phe Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
435                 440                 445

Leu Ser Leu Gly Lys
    450

<210> SEQ ID NO 23
<211> LENGTH: 456
<212> TYPE: PRT
<213> ORGANISM: Artificial Sequence
<220> FEATURE:
<223> OTHER INFORMATION: Heavy chain for 21F12-1B12

<400> SEQUENCE: 23

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455

<210> SEQ ID NO 24
<211> LENGTH: 453
<212> TYPE: PRT
<213> ORGANISM: Artificial Sequence
<220> FEATURE:
<223> OTHER INFORMATION: Heavy chain for 21F12-1B12

<400> SEQUENCE: 24

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ala Ser
            115                 120                 125

Thr Lys Gly Pro Ser Val Phe Pro Leu Ala Pro Cys Ser Arg Ser Thr
            130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly Lys
            450

<210> SEQ ID NO 25
<211> LENGTH: 456
<212> TYPE: PRT
<213> ORGANISM: Artificial Sequence
<220> FEATURE:
<223> OTHER INFORMATION: Heavy chain for 21F12-1E11

<400> SEQUENCE: 25

```
Gln Met Gln Leu Val Gln Ser Gly Ala Glu Lys Lys Pro Gly Ala
1               5                   10                  15

Ser Val Lys Leu Ser Cys Lys Ala Ser Gly Tyr Phe Phe Gln Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
            85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415
```

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455

<210> SEQ ID NO 26
<211> LENGTH: 453
<212> TYPE: PRT
<213> ORGANISM: Artificial Sequence
<220> FEATURE:
<223> OTHER INFORMATION: Heavy chain for 21F12-1E11

<400> SEQUENCE: 26

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Phe Phe Gln Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Ser Thr Thr Tyr Ala Gln Lys Phe
    50                  55                  60

Gln Gly Arg Val Thr Met Thr Arg Asp Thr Ser Ile Ser Thr Ala Tyr
65              70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser Ala Ser
            115                 120                 125

Thr Lys Gly Pro Ser Val Phe Pro Leu Ala Pro Cys Ser Arg Ser Thr
            130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Lys Thr Tyr Thr
            195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
            290                 295                 300

Thr Tyr Arg Val Val Ser Val Leu Thr Val Leu His Gln Asp Trp Leu
305                 310                 315                 320

```
Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 27
<211> LENGTH: 456
<212> TYPE: PRT
<213> ORGANISM: Artificial Sequence
<220> FEATURE:
<223> OTHER INFORMATION: Heavy chain for 21F12-2E1

<400> SEQUENCE: 27

Gln Met Gln Leu Val Gln Ser Gly Ala Glu Val Lys Lys Pro Gly Ala
1               5                   10                  15

Ser Val Lys Leu Ser Cys Lys Ala Ser Glu Tyr Ile Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

-continued

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Ala Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
            450                 455

<210> SEQ ID NO 28
<211> LENGTH: 453
<212> TYPE: PRT
<213> ORGANISM: Artificial Sequence
<220> FEATURE:
<223> OTHER INFORMATION: Heavy chain for 21F12-2E1

<400> SEQUENCE: 28

Gln Met Gln Leu Val Gln Ser Gly Ala Glu Val Lys Lys Pro Gly Ala
1               5                   10                  15

Ser Val Lys Leu Ser Cys Lys Ala Ser Glu Tyr Ile Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Cys Ser Arg Ser Thr
            130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 29
<211> LENGTH: 456
<212> TYPE: PRT
<213> ORGANISM: Artificial Sequence
<220> FEATURE:
<223> OTHER INFORMATION: Heavy chain for 21F12-2H7

<400> SEQUENCE: 29

Gln Met Gln Leu Val Gln Ser Gly Ala Glu Val Lys Lys Pro Gly Ala
1               5                   10                  15

Ser Val Lys Leu Ser Cys Lys Ala Ser Gln Tyr Ile Phe Gln Ser Tyr
            20                  25                  30

-continued

```
Tyr Ile His Trp Val Arg Gln Ala Pro Gly Gln Gly Leu Glu Trp Val
         35                  40                  45
Gly Val Ile Asn Pro Ser Gly Gly Ser Thr Thr Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Val Tyr Tyr Cys
                 85                  90                  95
Ala Arg Gly Ser Tyr Ser Ser Gly Trp Asp Tyr Tyr Tyr Tyr Gly
                100                 105                 110
Met Asp Val Trp Gly Lys Gly Thr Leu Val Thr Val Ser Ser Ala Ser
                115                 120                 125
Thr Lys Gly Pro Ser Val Phe Pro Leu Ala Pro Ser Ser Lys Ser Thr
    130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
                180                 185                 190
Ser Val Val Thr Val Pro Ser Ser Ser Leu Gly Thr Gln Thr Tyr Ile
        195                 200                 205
Cys Asn Val Asn His Lys Pro Ser Asn Thr Lys Val Asp Lys Lys Val
210                 215                 220
Glu Pro Lys Ser Cys Asp Lys Thr His Thr Cys Pro Pro Cys Pro Ala
225                 230                 235                 240
Pro Glu Ala Ala Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
                260                 265                 270
Val Ala Val Ser His Glu Asp Pro Glu Val Lys Phe Asn Trp Tyr Val
        275                 280                 285
Asp Gly Val Glu Val His Asn Ala Lys Thr Lys Pro Arg Glu Glu Gln
290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Ala Ala Pro Ile Glu Lys Thr Ile Ser Lys Ala Lys Gly Gln Pro
                340                 345                 350
Arg Glu Pro Gln Val Tyr Thr Leu Pro Pro Ser Arg Asp Glu Leu Thr
                355                 360                 365
Lys Asn Gln Val Ser Leu Thr Cys Leu Val Lys Gly Phe Tyr Pro Ser
370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
                420                 425                 430
Ser Cys Ser Val Met His Glu Ala Leu His Asn His Tyr Thr Gln Lys
                435                 440                 445
Ser Leu Ser Leu Ser Pro Gly Lys
```

<210> SEQ ID NO 30
<211> LENGTH: 453
<212> TYPE: PRT
<213> ORGANISM: Artificial Sequence
<220> FEATURE:
<223> OTHER INFORMATION: Heavy chain for 21F12-2H7

<400> SEQUENCE: 30

```
Gln Met Gln Leu Val Gln Ser Gly Ala Glu Val Lys Lys Pro Gly Ala
1               5                   10                  15

Ser Val Lys Leu Ser Cys Lys Ala Ser Gln Tyr Ile Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
```

```
                355                 360                 365
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 31
<211> LENGTH: 456
<212> TYPE: PRT
<213> ORGANISM: Artificial Sequence
<220> FEATURE:
<223> OTHER INFORMATION: Heavy chain for 21F12-1C4

<400> SEQUENCE: 31

Gln Met Gln Leu Val Gln Ser Gly Ala Glu Val Lys Lys Pro Gly Ala
1               5                   10                  15

Ser Val Lys Leu Ser Cys Lys Ala Ser Asp Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
```

```
                    260                 265                 270
Val Ala Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 32
<211> LENGTH: 453
<212> TYPE: PRT
<213> ORGANISM: Artificial Sequence
<220> FEATURE:
<223> OTHER INFORMATION: Heavy chain for 21F12-1C4

<400> SEQUENCE: 32

Gln Met Gln Leu Val Gln Ser Gly Ala Glu Val Lys Lys Pro Gly Ala
1               5                   10                  15

Ser Val Lys Leu Ser Cys Lys Ala Ser Asp Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
```

-continued

```
                165                 170                 175
His Thr Phe Pro Ala Val Leu Gln Ser Ser Gly Leu Tyr Ser Leu Ser
            180                 185                 190

Ser Val Val Thr Val Pro Ser Ser Leu Gly Thr Lys Thr Tyr Thr
            195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
            325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly Lys
            450
```

<210> SEQ ID NO 33
<211> LENGTH: 456
<212> TYPE: PRT
<213> ORGANISM: Artificial Sequence
<220> FEATURE:
<223> OTHER INFORMATION: Heavy chain for 21F12-1E10

<400> SEQUENCE: 33

```
Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Pro Phe Thr Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
```

```
            65                  70                  75                  80
        Met Glu Leu Ser Arg Leu Arg Ser Asp Asp Thr Val Val Tyr Tyr Cys
                        85                  90                  95

Ala Arg Gly Ser Tyr Ser Ser Gly Trp Asp Tyr Tyr Tyr Tyr Tyr Gly
                        100                 105                 110

Met Asp Val Trp Gly Lys Gly Thr Leu Val Thr Val Ser Ser Ala Ser
                        115                 120                 125

Thr Lys Gly Pro Ser Val Phe Pro Leu Ala Pro Ser Ser Lys Ser Thr
                        130                 135                 140

Ser Gly Gly Thr Ala Ala Leu Gly Cys Leu Val Lys Asp Tyr Phe Pro
        145                 150                 155                 160

Glu Pro Val Thr Val Ser Trp Asn Ser Gly Ala Leu Thr Ser Gly Val
                        165                 170                 175

His Thr Phe Pro Ala Val Leu Gln Ser Ser Gly Leu Tyr Ser Leu Ser
                        180                 185                 190

Ser Val Val Thr Val Pro Ser Ser Ser Leu Gly Thr Gln Thr Tyr Ile
                        195                 200                 205

Cys Asn Val Asn His Lys Pro Ser Asn Thr Lys Val Asp Lys Lys Val
                        210                 215                 220

Glu Pro Lys Ser Cys Asp Lys Thr His Thr Cys Pro Pro Cys Pro Ala
        225                 230                 235                 240

Pro Glu Ala Ala Gly Gly Pro Ser Val Phe Leu Phe Pro Pro Lys Pro
                        245                 250                 255

Lys Asp Thr Leu Met Ile Ser Arg Thr Pro Glu Val Thr Cys Val Val
                        260                 265                 270

Val Ala Val Ser His Glu Asp Pro Glu Val Lys Phe Asn Trp Tyr Val
                        275                 280                 285

Asp Gly Val Glu Val His Asn Ala Lys Thr Lys Pro Arg Glu Glu Gln
                        290                 295                 300

Tyr Asn Ser Thr Tyr Arg Val Val Ser Val Leu Thr Val Leu His Gln
        305                 310                 315                 320

Asp Trp Leu Asn Gly Lys Glu Tyr Lys Cys Lys Val Ser Asn Lys Ala
                        325                 330                 335

Leu Ala Ala Pro Ile Glu Lys Thr Ile Ser Lys Ala Lys Gly Gln Pro
                        340                 345                 350

Arg Glu Pro Gln Val Tyr Thr Leu Pro Pro Ser Arg Asp Glu Leu Thr
                        355                 360                 365

Lys Asn Gln Val Ser Leu Thr Cys Leu Val Lys Gly Phe Tyr Pro Ser
                        370                 375                 380

Asp Ile Ala Val Glu Trp Glu Ser Asn Gly Gln Pro Glu Asn Asn Tyr
        385                 390                 395                 400

Lys Thr Thr Pro Pro Val Leu Asp Ser Asp Gly Ser Phe Phe Leu Tyr
                        405                 410                 415

Ser Lys Leu Thr Val Asp Lys Ser Arg Trp Gln Gln Gly Asn Val Phe
                        420                 425                 430

Ser Cys Ser Val Met His Glu Ala Leu His Asn His Tyr Thr Gln Lys
                        435                 440                 445

Ser Leu Ser Leu Ser Pro Gly Lys
                450                 455

<210> SEQ ID NO 34
<211> LENGTH: 453
<212> TYPE: PRT
<213> ORGANISM: Artificial Sequence
```

<220> FEATURE:
<223> OTHER INFORMATION: Heavy chain for 21F12-1E10

<400> SEQUENCE: 34

```
Gln Met Gln Leu Val Gln Ser Gly Ala Glu Lys Lys Pro Gly Ala
1               5                   10                  15

Ser Val Lys Leu Ser Cys Lys Ala Ser Gly Tyr Pro Phe Thr Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Gly
                100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Lys Thr Tyr Thr
            195                 200                 205

Cys Asn Val Asp His Lys Pro Ser Asn Thr Lys Val Asp Lys Arg Val
            210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400
```

Pro Pro Val Leu Asp Ser Asp Gly Ser Phe Phe Leu Tyr Ser Arg Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly Lys
            450

<210> SEQ ID NO 35
<211> LENGTH: 456
<212> TYPE: PRT
<213> ORGANISM: Artificial Sequence
<220> FEATURE:
<223> OTHER INFORMATION: Heavy chain for 21F12-1F6

<400> SEQUENCE: 35

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Gln Ser Tyr
            20                  25                  30

Tyr Ile His Trp Val Arg Gln Ala Pro Gly Gln Gly Leu Glu Trp Val
            35                  40                  45

Gly Val Ile Asn Pro Ser Gly Gly Ser Thr Thr Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 36
<211> LENGTH: 453
<212> TYPE: PRT
<213> ORGANISM: Artificial Sequence
<220> FEATURE:
<223> OTHER INFORMATION: Heavy chain for 21F12-1F6

<400> SEQUENCE: 36

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Gln Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Ser Ser Gly Trp Asp Tyr Tyr Tyr Tyr Tyr Gly
            100                 105                 110

Met Asp Val Trp Gly Lys Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

```
Cys Asn Val Asp His Lys Pro Ser Asn Thr Lys Val Asp Lys Arg Val
            210                 215                 220

Glu Ser Lys Tyr Gly Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 37
<211> LENGTH: 456
<212> TYPE: PRT
<213> ORGANISM: Artificial Sequence
<220> FEATURE:
<223> OTHER INFORMATION: Heavy chain for 21F12-3G1

<400> SEQUENCE: 37

Gln Met Gln Leu Val Gln Ser Gly Ala Glu Val Lys Lys Pro Gly Ala
1               5                   10                  15

Ser Val Lys Leu Ser Cys Lys Ala Ser Gly Tyr Ile Phe Thr Ser Tyr
            20                  25                  30

Tyr Ile His Trp Val Arg Gln Ala Pro Gly Gln Gly Leu Glu Trp Val
        35                  40                  45

Gly Val Ile Asn Pro Ser Gly Gly Ser Thr Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Gly Ser Tyr Asn Ser Gly Trp Asp Tyr Tyr Tyr Tyr Tyr Gly
            100                 105                 110
```

```
Met Asp Val Trp Gly Lys Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Ala Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Ala Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 38
<211> LENGTH: 453
<212> TYPE: PRT
<213> ORGANISM: Artificial Sequence
<220> FEATURE:
<223> OTHER INFORMATION: Heavy chain for 21F12-3G1

<400> SEQUENCE: 38

Gln Met Gln Leu Val Gln Ser Gly Ala Glu Val Lys Lys Pro Gly Ala
1               5                   10                  15
```

```
Ser Val Lys Leu Ser Cys Lys Ala Ser Gly Tyr Ile Phe Thr Ser Tyr
             20                  25                  30
Tyr Ile His Trp Val Arg Gln Ala Pro Gly Gln Gly Leu Glu Trp Val
         35                  40                  45
Gly Val Ile Asn Pro Ser Gly Gly Ser Thr Thr Tyr Ala Gln Lys Phe
50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Val Val Tyr Tyr Cys
             85                  90                  95
Ala Arg Gly Ser Tyr Asn Ser Gly Trp Asp Tyr Tyr Tyr Tyr Tyr Gly
            100                 105                 110
Met Asp Val Trp Gly Lys Gly Thr Leu Val Thr Val Ser Ser Ala Ser
            115                 120                 125
Thr Lys Gly Pro Ser Val Phe Pro Leu Ala Pro Cys Ser Arg Ser Thr
        130                 135                 140
Ser Glu Ser Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Lys Thr Tyr Thr
        195                 200                 205
Cys Asn Val Asp His Lys Pro Ser Asn Thr Lys Val Asp Lys Arg Val
210                 215                 220
Glu Ser Lys Tyr Gly Pro Pro Cys Pro Pro Cys Pro Ala Pro Glu Phe
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser Gln Glu Asp Pro Glu Val Gln Phe Asn Trp Tyr Val Asp Gly Val
        275                 280                 285
Glu Val His Asn Ala Lys Thr Lys Pro Arg Glu Glu Gln Phe Asn Ser
290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Gly Leu Pro Ser
                325                 330                 335
Ser Ile Glu Lys Thr Ile Ser Lys Ala Lys Gly Gln Pro Arg Glu Pro
            340                 345                 350
Gln Val Tyr Thr Leu Pro Pro Ser Gln Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Arg Leu
                405                 410                 415
Thr Val Asp Lys Ser Arg Trp Gln Glu Gly Asn Val Phe Ser Cys Ser
            420                 425                 430
```

```
Val Met His Glu Ala Leu His Asn His Tyr Thr Gln Lys Ser Leu Ser
        435                 440                 445

Leu Ser Leu Gly Lys
    450

<210> SEQ ID NO 39
<211> LENGTH: 219
<212> TYPE: PRT
<213> ORGANISM: Artificial Sequence
<220> FEATURE:
<223> OTHER INFORMATION: Light chain for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 39

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Gln Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 40
<211> LENGTH: 15
<212> TYPE: DNA
<213> ORGANISM: Artificial Sequence
<220> FEATURE:
<223> OTHER INFORMATION: VH-CDR1 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 40
agctactaca tccac                                                15

<210> SEQ ID NO 41
<211> LENGTH: 51
<212> TYPE: DNA
<213> ORGANISM: Artificial Sequence
```

```
<220> FEATURE:
<223> OTHER INFORMATION: VH-CDR2 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 41
gtgattaacc cctccggcgg ctccaccacc tatgctcaga agttccaggg c            51

<210> SEQ ID NO 42
<211> LENGTH: 51
<212> TYPE: DNA
<213> ORGANISM: Artificial Sequence
<220> FEATURE:
<223> OTHER INFORMATION: VH-CDR3 for 21F12, 21F12-1B12, 21F12-1E11,
      21F12-2E1, 21F12-2H7, 21F12-1C4, 21F12-1E10, 21F12-1F6

<400> SEQUENCE: 42
ggctcctact cctccggctg ggattactac tattactacg gcatggacgt g            51

<210> SEQ ID NO 43
<211> LENGTH: 51
<212> TYPE: DNA
<213> ORGANISM: Artificial Sequence
<220> FEATURE:
<223> OTHER INFORMATION: VH-CDR3 for 21F12-3G1

<400> SEQUENCE: 43
ggctcctaca actccggctg ggattactac tattactacg gcatggacgt g            51

<210> SEQ ID NO 44
<211> LENGTH: 378
<212> TYPE: DNA
<213> ORGANISM: Artificial Sequence
<220> FEATURE:
<223> OTHER INFORMATION: VH for 21F12

<400> SEQUENCE: 44
cagatgcagc tggtgcagtc cggcgccgag gtgaagaagc tggcgcttc cgtgaagctg    60 tcctgtaagg cctccggcta catcttcacc agctactaca tccactgggt gaggcaggct   120
cccggacagg gactggaatg ggtgggcgtg attaacccct ccggcggctc caccacctat   180
gctcagaagt tccagggcag ggtgaccatg accagggaca cctccatctc caccgcctac   240
atggagctgt ccaggctgag gtccgacgac accgtggtgt actactgcgc taggggctcc   300
tactcctccg gctgggatta ctactattac tacggcatgg acgtgtgggg caagggcacc   360
ctggtgaccg tgagctcc                                                378

<210> SEQ ID NO 45
<211> LENGTH: 378
<212> TYPE: DNA
<213> ORGANISM: Artificial Sequence
<220> FEATURE:
<223> OTHER INFORMATION: VH for 21F12-1B12

<400> SEQUENCE: 45
cagatgcagc tggtgcagtc cggcgccgag gtgaagaagc tggcgcttc cgtgaagctg    60 tcctgtaagg cctccggcta ccccttccag agctactaca tccactgggt gaggcaggct   120
cccggacagg gactggaatg ggtgggcgtg attaacccct ccggcggctc caccacctat   180
gctcagaagt tccagggcag ggtgaccatg accagggaca cctccatctc caccgcctac   240
atggagctgt ccaggctgag gtccgacgac accgtggtgt actactgcgc taggggctcc   300
tactcctccg gctgggatta ctactattac tacggcatgg acgtgtgggg caagggcacc   360
```
ctggtgaccg tgagctcc                                                  378

<210> SEQ ID NO 46
<211> LENGTH: 378
<212> TYPE: DNA
<213> ORGANISM: Artificial Sequence
<220> FEATURE:
<223> OTHER INFORMATION: VH for 21F12-1E11

<400> SEQUENCE: 46
cagatgcagc tggtgcagtc cggcgccgag gtgaagaagc tggcgcttc cgtgaagctg      60
tcctgtaagg cctccggcta cttcttccag agctactaca tccactgggt gaggcaggct    120
cccggacagg gactggaatg ggtgggcgtg attaacccct ccggcggctc caccacctat    180
gctcagaagt tccagggcag ggtgaccatg accaggaca cctccatctc caccgcctac     240
atggagctgt ccaggctgag gtccgacgac accgtggtgt actactgcgc tagggggctcc   300
tactcctccg gctgggatta ctactattac tacggcatgg acgtgtgggg caagggcacc    360
ctggtgaccg tgagctcc                                                  378

<210> SEQ ID NO 47
<211> LENGTH: 378
<212> TYPE: DNA
<213> ORGANISM: Artificial Sequence
<220> FEATURE:
<223> OTHER INFORMATION: VH for 21F12-2E1

<400> SEQUENCE: 47
cagatgcagc tggtgcagtc cggcgccgag gtgaagaagc tggcgcttc cgtgaagctg      60
tcctgtaagg cctccgagta catcttccag agctactaca tccactgggt gaggcaggct    120
cccggacagg gactggaatg ggtgggcgtg attaacccct ccggcggctc caccacctat    180
gctcagaagt tccagggcag ggtgaccatg accaggaca cctccatctc caccgcctac     240
atggagctgt ccaggctgag gtccgacgac accgtggtgt actactgcgc tagggggctcc   300
tactcctccg gctgggatta ctactattac tacggcatgg acgtgtgggg caagggcacc    360
ctggtgaccg tgagctcc                                                  378

<210> SEQ ID NO 48
<211> LENGTH: 378
<212> TYPE: DNA
<213> ORGANISM: Artificial Sequence
<220> FEATURE:
<223> OTHER INFORMATION: VH for 21F12-2H7

<400> SEQUENCE: 48
cagatgcagc tggtgcagtc cggcgccgag gtgaagaagc tggcgcttc cgtgaagctg      60
tcctgtaagg cctcccagta catcttccag agctactaca tccactgggt gaggcaggct    120
cccggacagg gactggaatg ggtgggcgtg attaacccct ccggcggctc caccacctat    180
gctcagaagt tccagggcag ggtgaccatg accaggaca cctccatctc caccgcctac     240
atggagctgt ccaggctgag gtccgacgac accgtggtgt actactgcgc tagggggctcc   300
tactcctccg gctgggatta ctactattac tacggcatgg acgtgtgggg caagggcacc    360
ctggtgaccg tgagctcc                                                  378

<210> SEQ ID NO 49
<211> LENGTH: 378
<212> TYPE: DNA

<213> ORGANISM: Artificial Sequence
<220> FEATURE:
<223> OTHER INFORMATION: VH for 21F12-1C4

<400> SEQUENCE: 49

| | | | | | |
|---|---|---|---|---|---|
| cagatgcagc | tggtgcagtc | cggcgccgag | gtgaagaagc | ctggcgcttc | cgtgaagctg | 60 |
| tcctgtaagg | cctccgacta | catcttcacc | agctactaca | tccactgggt | gaggcaggct | 120 |
| cccggacagg | gactggaatg | ggtgggcgtg | attaacccct | ccggcggctc | caccacctat | 180 |
| gctcagaagt | tccagggcag | ggtgaccatg | accagggaca | cctccatctc | caccgcctac | 240 |
| atggagctgt | ccaggctgag | gtccgacgac | accgtggtgt | actactgcgc | tagggggctcc | 300 |
| tactcctccg | gctgggatta | ctactattac | tacggcatgg | acgtgtgggg | caagggcacc | 360 |
| ctggtgaccg | tgagctcc | | | | | 378 |

<210> SEQ ID NO 50
<211> LENGTH: 378
<212> TYPE: DNA
<213> ORGANISM: Artificial Sequence
<220> FEATURE:
<223> OTHER INFORMATION: VH for 21F12-1E10

<400> SEQUENCE: 50

| | | | | | |
|---|---|---|---|---|---|
| cagatgcagc | tggtgcagtc | cggcgccgag | gtgaagaagc | ctggcgcttc | cgtgaagctg | 60 |
| tcctgtaagg | cctccggcta | ccctttcacc | agctactaca | tccactgggt | gaggcaggct | 120 |
| cccggacagg | gactggaatg | ggtgggcgtg | attaacccct | ccggcggctc | caccacctat | 180 |
| gctcagaagt | tccagggcag | ggtgaccatg | accagggaca | cctccatctc | caccgcctac | 240 |
| atggagctgt | ccaggctgag | gtccgacgac | accgtggtgt | actactgcgc | tagggggctcc | 300 |
| tactcctccg | gctgggatta | ctactattac | tacggcatgg | acgtgtgggg | caagggcacc | 360 |
| ctggtgaccg | tgagctcc | | | | | 378 |

<210> SEQ ID NO 51
<211> LENGTH: 378
<212> TYPE: DNA
<213> ORGANISM: Artificial Sequence
<220> FEATURE:
<223> OTHER INFORMATION: VH for 21F12-1F6

<400> SEQUENCE: 51

| | | | | | |
|---|---|---|---|---|---|
| cagatgcagc | tggtgcagtc | cggcgccgag | gtgaagaagc | ctggcgcttc | cgtgaagctg | 60 |
| tcctgtaagg | cctccggcta | catcttccag | agctactaca | tccactgggt | gaggcaggct | 120 |
| cccggacagg | gactggaatg | ggtgggcgtg | attaacccct | ccggcggctc | caccacctat | 180 |
| gctcagaagt | tccagggcag | ggtgaccatg | accagggaca | cctccatctc | caccgcctac | 240 |
| atggagctgt | ccaggctgag | gtccgacgac | accgtggtgt | actactgcgc | tagggggctcc | 300 |
| tactcctccg | gctgggatta | ctactattac | tacggcatgg | acgtgtgggg | caagggcacc | 360 |
| ctggtgaccg | tgagctcc | | | | | 378 |

<210> SEQ ID NO 52
<211> LENGTH: 378
<212> TYPE: DNA
<213> ORGANISM: Artificial Sequence
<220> FEATURE:
<223> OTHER INFORMATION: VH for 21F12-3G1

<400> SEQUENCE: 52

| | | | | | |
|---|---|---|---|---|---|
| cagatgcagc | tggtgcagtc | cggcgccgag | gtgaagaagc | ctggcgcttc | cgtgaagctg | 60 | tcctgtaagg cctccggcta catcttcacc agctactaca tccactgggt gaggcaggct    120 cccggacagg gactggaatg ggtgggcgtg attaacccct ccggcggctc caccacctat    180 gctcagaagt tccagggcag ggtgaccatg accagggaca cctccatctc caccgcctac    240 atggagctgt ccaggctgag gtccgacgac accgtggtgt actactgcgc tagggggctcc    300 tacaactccg gctgggatta ctactattac tacggcatgg acgtgtgggg caagggcacc    360 ctggtgaccg tgagctcc                                                 378

<210> SEQ ID NO 53
<211> LENGTH: 48
<212> TYPE: DNA
<213> ORGANISM: Artificial Sequence
<220> FEATURE:
<223> OTHER INFORMATION: VL-CDR1 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 53
cgctccagcc agtccctgct gcacagccag ggctacaatt atctggat                 48

<210> SEQ ID NO 54
<211> LENGTH: 21
<212> TYPE: DNA
<213> ORGANISM: Artificial Sequence
<220> FEATURE:
<223> OTHER INFORMATION: VL-CDR2 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 54
ctgggctcta acagggcctc c                                              21

<210> SEQ ID NO 55
<211> LENGTH: 27
<212> TYPE: PRT
<213> ORGANISM: Artificial Sequence
<220> FEATURE:
<223> OTHER INFORMATION: VL-CDR3 for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 55

Ala Thr Gly Cys Ala Gly Gly Cys Thr Cys Thr Gly Cys Ala Gly Ala
1               5                   10                  15

Cys Cys Cys Cys Ala Thr Gly Gly Ala Cys Ala
            20                  25

<210> SEQ ID NO 56
<211> LENGTH: 336
<212> TYPE: DNA
<213> ORGANISM: Artificial Sequence
<220> FEATURE:
<223> OTHER INFORMATION: VL for 21F12, 21F12-1B12, 21F12-1E11, 21F12-
      2E1, 21F12-2H7, 21F12-1C4, 21F12-1E10, 21F12-1F6, and 21F12-3G1

<400> SEQUENCE: 56
gacgtggtca tgacccagag cccactgtct ctgccagtga cacctggaga gccagcttct    60
atctcctgcc gctccagcca gtccctgctg cacagccagg gctacaatta tctggattgg    120
tacctgcaga agcccggcca gtcccctcag ctgctgatct atctgggctc taacagggcc    180
tccggagtgc ctgaccggtt tagcggctct ggctccggca ccgatttcac actgaagatc    240
tccagggtgg aggctgagga cgtgggcgtg tactattgta tgcaggctct gcagaccccca    300

```
tggacatttg ccagggcac aaaggtggag atcaag                                    336
```

<210> SEQ ID NO 57
<211> LENGTH: 993
<212> TYPE: DNA
<213> ORGANISM: Artificial Sequence
<220> FEATURE:
<223> OTHER INFORMATION: Mutant IgG1 CH for 21F12, 21F12-1B12, 21F12-
      1E11, 21F12-2E1, 21F12-2H7, 21F12-1C4, 21F12-1E10, 21F12-1F6, and
      21F12-3G1

<400> SEQUENCE: 57

```
gctagcacca agggaccatc cgtgttccca ctggccccct ccagcaagtc caccagcgga     60
ggaacagccg ctctgggatg cctggtgaag gactacttcc cagagcccgt gacagtgagc    120
tggaactctg gcgccctgac cagcggagtg cacacatttc cgccgtgct ccagtcttcc     180
ggcctgtact ctctgagctc tgtggtgacc gtgccctcca gctctctggg cacccagaca    240
tatatctgca acgtgaatca caagccaagc aatacaaagg tggacaagaa ggtggagccc    300
aagtcttgtg ataagaccca tacatgcccc ccttgtcctg ctccagaggc tgctggagga    360
ccaagcgtgt tcctgtttcc acccaagcct aaggacaccc tgatgatctc caggaccccc    420
gaggtgacat gcgtggtggt ggctgtgagc cacgaggacc ccgaggtgaa gtttaactgg    480
tacgtggatg gcgtggaggt gcataatgct aagaccaagc taggagga gcagtacaac     540
tctacctatc gggtggtgtc cgtgctgaca gtgctgcacc aggactggct gaacggcaag    600
gagtataagt gcaaggtgtc taataaggcc ctggctgctc ctatcgagaa gaccatctcc    660
aaggccaagg gccagcctag agagccacag gtgtacacac tgcctccatc tcgcgacgag    720
ctgaccaaga accaggtgtc cctgacatgt ctggtgaagg gcttctatcc ttccgacatc    780
gctgtggagt gggagagcaa cggccagcca gagaacaatt acaagaccac cccctgtg    840
ctggactccg atggcagctt ctttctgtat agcaagctga ccgtggataa gtccaggtgg    900
cagcagggca acgtgttttc ttgctccgtg atgcatgagg ctctgcacaa tcattataca    960
cagaagagcc tgtctctgtc ccctggcaag tga                                 993
```

<210> SEQ ID NO 58
<211> LENGTH: 984
<212> TYPE: DNA
<213> ORGANISM: Artificial Sequence
<220> FEATURE:
<223> OTHER INFORMATION: IgG4 CH for 21F12, 21F12-1B12, 21F12-1E11,
      21F12-2E1, 21F12-2H7, 21F12-1C4, 21F12-1E10, 21F12-1F6, and
      21F12-3G1

<400> SEQUENCE: 58

```
gctagcacaa agggaccttc cgtgttccca ctggccccct gctccagaag cacatctgag     60
tccaccgccg ctctgggctg tctggtgaag gactacttcc ctgagccagt gaccgtgtcc    120
tggaacagcg gcgccctgac atccggagtg cacacctttc cgccgtgct ccagtccagc     180
ggactgtaca gcctgtcttc cgtggtgaca gtgcccagct cttccctggg caccaagaca    240
tatacctgca acgtggacca taagcctagc aataccaagg tggataagag ggtggagtct    300
aagtacggac accttgcccc accatgtcca gctcctgagt ttctgggagg accatccgtg    360
ttcctgtttc ctccaaagcc taaggacacc ctgatgatct ctcggacacc tgaggtgacc    420
tgcgtggtgg tggacgtgtc ccaggaggac cccgaggtgc agttcaactg gtacgtggat    480
ggcgtggagg tgcacaatgc taagaccaag ccaagagagg agcagtttaa tagcacatac    540
```

```
cgcgtggtgt ctgtgctgac cgtgctgcat caggattggc tgaacggcaa ggagtataag    600
tgcaaggtga gcaataaggg cctgcccagc tctatcgaga agacaatctc taaggctaag    660
ggacagcctc gcgagccaca ggtgtacacc ctgcccccct cccaggagga gatgacaaag    720
aaccaggtga gcctgacctg tctggtgaag ggcttctatc catctgacat cgctgtggag    780
tgggagtcca acggccagcc cgagaacaat tacaagacca ccaccccgt gctggactct    840 gatggctcct tctttctgta ttccaggctg acagtggata gagccggtg gcaggagggc    900 aacgtgttta gctgctctgt gatgcacgag gctctgcaca atcattatac ccagaagtcc    960
ctgagcctgt ctctgggcaa gtaa                                           984

<210> SEQ ID NO 59
<211> LENGTH: 324
<212> TYPE: DNA
<213> ORGANISM: Artificial Sequence
<220> FEATURE:
<223> OTHER INFORMATION: CL for 21F12, 21F12-1B12, 21F12-1E11, 21F12-
      2E1, 21F12-2H7, 21F12-1C4, 21F12-1E10, 21F12-1F6, and 21F12-3G1

<400> SEQUENCE: 59
cgtacggtgg ctgcaccatc tgtcttcatc ttcccgccat ctgatgagca gttgaaatct    60
ggaactgcct ctgttgtgtg cctgctgaat aacttctacc ccagagaagc caaagtgcag   120
tggaaggtgg acaacgccct gcagagcgga aacagccagg aaagcgtgac agagcaggat   180
tccaaggatt ccacatacag cctgagcagc acactgacac tgtccaaggc cgactacgag   240
aagcacaagg tgtacgcctg cgaagtgaca caccagggac tgtcctcccc tgtgacaaag   300
agcttcaaca gaggagaatg ctga                                          324

<210> SEQ ID NO 60
<211> LENGTH: 15
<212> TYPE: PRT
<213> ORGANISM: Artificial Sequence
<220> FEATURE:
<223> OTHER INFORMATION: Linker

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 439
<212> TYPE: PRT
<213> ORGANISM: Artificial Sequence
<220> FEATURE:
<223> OTHER INFORMATION: Heavy chain for human IgG control

<400> SEQUENCE: 61

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Ser Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Thr Gly Gly Tyr Trp Gly Gln Gly Thr Leu Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly Lys
            435

<210> SEQ ID NO 62
<211> LENGTH: 215
<212> TYPE: PRT
<213> ORGANISM: Artificial Sequence
<220> FEATURE:
<223> OTHER INFORMATION: Light chain for human IgG control

<400> SEQUENCE: 62

Asp Ile Arg Leu Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Ser Thr Pro Tyr
                85                  90                  95

Thr Phe Gly Gln Gly Thr Lys Leu Thr Val Leu Gly Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 63
<211> LENGTH: 440
<212> TYPE: PRT
<213> ORGANISM: Artificial Sequence
<220> FEATURE:
<223> OTHER INFORMATION: Heavy chain for Nivolumab analog

<400> SEQUENCE: 63

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160
```

```
Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 64
<211> LENGTH: 214
<212> TYPE: PRT
<213> ORGANISM: Artificial Sequence
<220> FEATURE:
<223> OTHER INFORMATION: Light chain for Nivolumab analog

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 465
<212> TYPE: PRT
<213> ORGANISM: Artificial Sequence
<220> FEATURE:
<223> OTHER INFORMATION: Human PD-L1-mouse Fc-tag

<400> SEQUENCE: 65

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220
```

-continued

Val Ile Pro Glu Leu Pro Leu Ala His Pro Pro Asn Glu Arg Val Pro
225                 230                 235                 240

Arg Asp Cys Gly Cys Lys Pro Cys Ile Cys Thr Val Pro Glu Val Ser
            245                 250                 255

Ser Val Phe Ile Phe Pro Pro Lys Pro Lys Asp Val Leu Thr Ile Thr
            260                 265                 270

Leu Thr Pro Lys Val Thr Cys Val Val Asp Ile Ser Lys Asp Asp
        275                 280                 285

Pro Glu Val Gln Phe Ser Trp Phe Val Asp Asp Val Glu Val His Thr
    290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
            325                 330                 335

Phe Lys Cys Arg Val Asn Ser Ala Ala Phe Pro Ala Pro Ile Glu Lys
            340                 345                 350

Thr Ile Ser Lys Thr Lys Gly Arg Pro Lys Ala Pro Gln Val Tyr Thr
        355                 360                 365

Ile Pro Pro Pro Lys Glu Gln Met Ala Lys Asp Lys Val Ser Leu Thr
370                 375                 380

Cys Met Ile Thr Asp Phe Phe Pro Glu Asp Ile Thr Val Glu Trp Gln
385                 390                 395                 400

Trp Asn Gly Gln Pro Ala Glu Asn Tyr Lys Asn Thr Gln Pro Ile Met
            405                 410                 415

Asp Thr Asp Gly Ser Tyr Phe Val Tyr Ser Lys Leu Asn Val Gln Lys
            420                 425                 430

Ser Asn Trp Glu Ala Gly Asn Thr Phe Thr Cys Ser Val Leu His Glu
        435                 440                 445

Gly Leu His Asn His His Thr Glu Lys Ser Leu Ser His Ser Pro Gly
    450                 455                 460

Lys
465

<210> SEQ ID NO 66
<211> LENGTH: 288
<212> TYPE: PRT
<213> ORGANISM: Artificial Sequence
<220> FEATURE:
<223> OTHER INFORMATION: Human PD-1

<400> SEQUENCE: 66

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

```
Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285
```

<210> SEQ ID NO 67
<211> LENGTH: 290
<212> TYPE: PRT
<213> ORGANISM: Artificial Sequence
<220> FEATURE:
<223> OTHER INFORMATION: Human PD-L1

<400> SEQUENCE: 67

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190
```

```
Val Thr Ser Thr Leu Arg Ile Asn Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 68
<211> LENGTH: 367
<212> TYPE: PRT
<213> ORGANISM: Artificial Sequence
<220> FEATURE:
<223> OTHER INFORMATION: OKT3-scFv

<400> SEQUENCE: 68

Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
                20                  25                  30

Pro Gly Ala Ser Val Lys Met Ser Cys Lys Ala Ser Gly Tyr Thr Phe
            35                  40                  45

Thr Arg Tyr Thr Met His Trp Val Lys Gln Arg Pro Gly Gln Gly Leu
        50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Tyr Tyr Asp Asp His Tyr Cys Leu Asp Tyr Trp
            115                 120                 125

Gly Gln Gly Thr Thr Leu Thr Val Ser Ser Gly Gly Gly Gly Ser Gly
        130                 135                 140

Gly Gly Gly Ser Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
                180                 185                 190

Gly Thr Ser Pro Lys Arg Trp Ile Tyr Asp Thr Ser Lys Leu Ala Ser
            195                 200                 205

Gly Val Pro Ala His Phe Arg Gly Ser Gly Ser Gly Thr Ser Tyr Ser
        210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255
```

```
Glu Ile Asn Ser Ser Val Val Pro Val Leu Gln Lys Val Asn Ser Thr
            260                 265                 270

Thr Thr Lys Pro Val Leu Arg Thr Pro Ser Pro Val His Pro Thr Gly
        275                 280                 285

Thr Ser Gln Pro Gln Arg Pro Glu Asp Cys Arg Pro Arg Gly Ser Val
    290                 295                 300

Lys Gly Thr Gly Leu Asp Phe Ala Cys Asp Ile Tyr Ile Trp Ala Pro
305                 310                 315                 320

Leu Ala Gly Ile Cys Val Ala Leu Leu Ser Leu Ile Ile Thr Leu
            325                 330                 335

Ile Cys Tyr His Arg Ser Arg Lys Arg Val Cys Lys Cys Pro Arg Pro
            340                 345                 350

Leu Val Arg Gln Glu Gly Lys Pro Arg Pro Ser Glu Lys Ile Val
        355                 360                 365
```

<210> SEQ ID NO 69
<211> LENGTH: 451
<212> TYPE: PRT
<213> ORGANISM: Artificial Sequence
<220> FEATURE:
<223> OTHER INFORMATION: Heavy chain for Rituximab analog

<400> SEQUENCE: 69

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
        340                 345                 350
Tyr Thr Leu Pro Pro Ser Arg Asp Glu Leu Thr Lys Asn Gln Val Ser
    355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
        420                 425                 430
His Glu Ala Leu His Asn His Tyr Thr Gln Lys Ser Leu Ser Leu Ser
    435                 440                 445
Pro Gly Lys
    450

<210> SEQ ID NO 70
<211> LENGTH: 213
<212> TYPE: PRT
<213> ORGANISM: Artificial Sequence
<220> FEATURE:
<223> OTHER INFORMATION: Light chain for Rituximab analog

<400> SEQUENCE: 70

Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Ser Val Ser Tyr Ile
            20                  25                  30
His Trp Phe Gln Gln Lys Pro Gly Ser Ser Pro Lys Pro Trp Ile Tyr
        35                  40                  45
Ala Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 71
<211> LENGTH: 386
<212> TYPE: PRT
<213> ORGANISM: Artificial Sequence
<220> FEATURE:
<223> OTHER INFORMATION: Ovalbumin

<400> SEQUENCE: 71

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300
```

```
Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
            325                 330                 335

Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
            355                 360                 365

Ile Lys His Ile Ala Thr Asn Ala Val Leu Phe Phe Gly Arg Cys Val
    370                 375                 380

Ser Pro
385
```

ANTIBODY BINDING PD-1 AND USE THEREOF

RELATED APPLICATIONS

This application claims the benefit under 35 U.S.C. § 119(e) of U.S. provisional application No. 62/672,602, filed May 17, 2018, the entire contents of which are incorporated herein by reference.

TECHNICAL FIELD

The present invention relates generally to an isolated monoclonal antibody, particularly a monoclonal antibody that specifically binds to human PD-1 with high affinity and functionality. A nucleic acid molecule encoding the antibody, an expression vector, a host cell and a method for expressing the antibody are also provided. The present invention further provides an immunoconjugate, a bispecific molecule and a pharmaceutical composition comprising the antibody, as well as a diagnostic and treatment method using an anti-PD-1 antibody of the invention.

BACKGROUND

Therapeutic antibodies are one of the fastest growing segments of the pharmaceutical industry, especially monoclonal antibodies targeting certain disease-related cellular proteins.

One such target protein is programmed cell death protein 1, also known as PD-1 (CD279), encoded by the PDCD1 gene (Ishida Y, et al., *EMBO J* 11:3887-95(1992); Francisco L M, et al., *Immunological Reviews.* 236: 219-42 (2010)), which is a member of the CD28 family of T cell regulators but exists as a monomer, lacking the unpaired cysteine residue characteristic in other CD28 family members.

The PD-1 is a 55 kDa type I transmembrane protein that belongs to the immunoglobulin superfamily and is expressed on activated B cells, T cells, and myeloid cells (Keir M E, et al., *Annu Rev Immunol* 26:677-704(2008); Agata et al. (1996) *Int Immunol* 8:765-72; Okazaki et al. (2002) *Curr. Opin. Immunol.* 14: 391779-82; Bennett et al. (2003) *J Immunol* 170:711-8). PD-1 binds two ligands, PD-L1 and PD-L2 (Dong H, et al., *Nat Med* 5:1365-9(1999); LatchmanY, et al., *Nat Immunol* 2:261-8(2001)). Upon binding to its ligands, PD-1 is found to inhibit signaling of the T-cell receptor (TCR), and downregulate the secretion of immunostimulatory cytokines and expression of survival proteins (Keir M E, et al., *Annu Rev Immunol* 26:677-704 (2008); Dong H, et al., *Nat Med* 5:1365-9(1999)).

Preclinical studies showed tumor regression or prolonged host survival after abrogation of PD-1 pathway signaling alone (Hirano F, et al., *Cancer Res* 65:1089-96(2005)) or in combination with other immune checkpoint inhibition (Woo S R, et al., *Cancer Res* 72(4):917-27(2012)).

A number of cancer immunotherapy agents that target the PD-1 receptor have been developed. One such anti-PD-1 antibody is Nivolumab (sold under the tradename of OPDIVO® by Bristol Myers Squibb), which produced complete or partial responses in non-small-cell lung cancer, melanoma, and renal-cell cancer, in a clinical trial with a total of 296 patients (Topalian S L et al. (2012) *The New England Journal of Medicine.* 366 (26): 2443-54). It was approved in Japan in 2014 and by US FDA in 2014 to treat metastatic melanoma. Another anti-PD-1 antibody, Pembrolizumab (KEYTRUDA™, MK-3475, Merck) targeting PD-1 receptors, was also approved by US FDA in 2014 to treat metastatic melanoma. It is being used in clinical trials in US for lung cancer, lymphoma, and mesothelioma.

Despite the anti-PD-1 antibodies that are already developed and approved, there is a need for additional monoclonal antibodies with enhanced binding affinity and other desirable pharmaceutical characteristics.

SUMMARY OF THE INVENTION

The present invention provides an isolated monoclonal antibody, for example, a human monoclonal antibody, that binds to human or monkey PD-1.

In one aspect, the invention pertains to an isolated monoclonal antibody (e.g., a human antibody), or an antigen-binding portion thereof, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, 99% or 100% identity to (1) SEQ ID NOs: 1, 2 and 3, respectively; or
(2) SEQ ID NOs: 1, 2 and 4, respectively;

wherein the antibody or antigen-binding fragment thereof binds PD-1. Theses amino acid sequences may be encoded by nucleic acid sequences of SEQ ID NOs: 40 to 43, respectively.

In one aspect, an isolated monoclonal antibody (e.g., a human antibody), or an antigen-binding portion thereof, of the present invention comprises a heavy chain variable region comprising an amino acid sequence having at least 80%, 85%, 90%, 95%, 98%, 99% or 100% identity to any one of SEQ ID NOs: 8 to 16, wherein the antibody or antigen-binding fragment thereof binds PD-1. These amino acid sequences may be encoded by nucleic acid sequences of SEQ ID NOs: 44 to 52, respectively.

The monoclonal antibody or an antigen-binding portion thereof of the present invention in one embodiment comprises a light chain variable region that comprises a CDR1 region, a CDR2 region and a CDR3 region, wherein the CDR1 region, the CDR2 region, and the CDR3 region comprise amino acid sequences having at least 80%, 85%, 90%, 95%, 98%, 99% or 100% identity to SEQ ID NOs: 5, 6 and 7, respectively, wherein the antibody or antigen-binding fragment thereof binds PD-1. Theses amino acid sequences may be encoded by nucleic acid sequences of SEQ ID NOs: 53 to 55, respectively.

In one aspect, an isolated monoclonal antibody (e.g., a human antibody), or an antigen-binding portion thereof, of the present invention comprises a light chain variable region comprising an amino acid sequence having at least 80%, 85%, 90%, 95%, 98%, 99% or 100% identity to SEQ ID NO: 17, wherein the antibody or antigen-binding fragment thereof binds PD-1. These amino acid sequences may be encoded by nucleic acid sequence of SEQ ID NO: 56.

In one aspect, an isolated monoclonal antibody, or an antigen-binding portion thereof, of the present invention comprises a heavy chain variable region and a light chain variable region each comprises a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 85%, 90%, 95%, 98%, 99% or 100% identity to (1) SEQ ID NOs: 1, 2, 3, 5, 6 and 7, respectively; or (2) SEQ ID NOs: 1, 2, 4, 5, 6 and 7, respectively, wherein the antibody or antigen-binding fragment thereof binds to PD-1.

In one embodiment, the antibody, or the antigen-binding portion thereof, comprises a heavy chain variable region and a light chain variable region, the heavy chain variable region and the light chain variable region comprising amino acid sequences having at least 80%, 85%, 90%, 95%, 98%, 99% or 100% identity to (1) SEQ ID NOs: 8 and 17, respectively; (2) SEQ ID NOs: 9 and 17, respectively; (3) SEQ ID NOs: 10 and 17, respectively; (4) SEQ ID NOs: 11 and 17, respectively; (5) SEQ ID NOs: 12 and 17, respectively; (6) SEQ ID NOs: 13 and 17, respectively; (7) SEQ ID NOs: 14 and 17, respectively; (8) SEQ ID NOs: 15 and 17, respectively; or (9) SEQ ID NOs: 16 and 17, respectively, wherein the antibody or antigen-binding fragment thereof binds PD-1.

In one embodiment, the antibody, or the antigen-binding thereof, comprises a heavy chain and a light chain, wherein the heavy chain comprises a heavy chain variable region as described above and a heavy chain constant region set forth in SEQ ID NOs.: 18 or 19, and the light chain comprises a light chain variable region as described above and a light chain constant region set forth in SEQ ID NO.: 20. The amino acid sequences of SEQ ID NOs: 18 to 20 may be encoded by nucleic acid sequences of SEQ ID NOs: 57 to 59.

In one embodiment, the antibody, or the antigen-binding portion thereof, comprises a heavy chain and a light chain, interconnected by disulfide bonds, which comprising amino acid sequences having at least 80%, 85%, 90%, 95%, 98%, 99% or 100% identity to (1) SEQ ID NOs: 21 and 39, respectively; (2) SEQ ID NOs: 22 and 39, respectively; (3) SEQ ID NOs: 23 and 39, respectively; (4) SEQ ID NOs: 24 and 39, respectively; (5) SEQ ID NOs: 25 and 39, respectively; (6) SEQ ID NOs: 26 and 39, respectively; (7) SEQ ID NOs: 27 and 39, respectively; (8) SEQ ID NOs: 28 and 39, respectively; (9) SEQ ID NOs: 29 and 39, respectively; (10) SEQ ID NOs: 30 and 39, respectively; (11) SEQ ID NOs: 31 and 39, respectively; (12) SEQ ID NOs: 32 and 39, respectively; (13) SEQ ID NOs: 33 and 39, respectively; (14) SEQ ID NOs: 34 and 39, respectively; (15) SEQ ID NOs: 35 and 39, respectively; (16) SEQ ID NOs: 36 and 39, respectively; (17) SEQ ID NOs: 37 and 39, respectively; or (18) SEQ ID NOs: 38 and 39, respectively, wherein the antibody or antigen-binding fragment thereof binds PD-1.

The antibody, or the antigen-binding portion thereof, of the invention has comparable or even better binding affinity/capacity to human PD-1 or monkey PD-1 as compared to prior art anti-PD-1 antibodies such as Nivolumab. Further, the antibody, or the antigen-binding portion thereof, of the invention induces T cells to release more IL-2 and IFNγ, and provides better in vivo anti-tumor effect, than prior art anti-PD-1 antibodies such as Nivolumab.

In specific, the antibody, or the antigen-binding portion thereof, of the invention binds to human PD-1 with a $K_D$ of approximately $1.406 \times 10^{-9}$ M or less and inhibits the binding of PD-L1/PD-L2 to PD-1. The antibody, or the antigen-binding portion thereof, of the invention does not bind to mouse PD-1, and does not cross react with CD28, ICOS, BTLA or CTLA-4. Further, the antibody, or the antigen-binding portion thereof, of the invention binds to cynomolgus monkey PD-1 with a lower $EC_{50}$ value, and induces T cells release higher levels of IL-2 secretion and IFNγ, than prior art anti-PD-1 antibodies such as Nivolumab. The antibody, or the antigen-binding portion thereof, of the invention stimulates antigen-specific memory responses, and/or stimulates antibody responses.

The antibodies of the invention can be, for example, full-length antibodies, for example of an IgG1 or IgG4 isotype. Alternatively, the antibodies can be antibody fragments, such as Fab or F(ab')2 fragments, or single chain antibodies. The heavy chain constant region is specially designed such that the anti-PD-1 antibody does not induce Antibody-Dependent Cell-Mediated Cytotoxicity (ADCC) or Complement-Dependent Cytotoxicity (CDC) on PD-1 expressing cells. For example, human IgG1 heavy chain may contain L234A, L235A, D265A and/or P329A (EU numbering) mutations for elimination of ADCC or CDC function. The antibodies of the invention can be mouse, chimeric, human or humanized antibodies, such as monoclonal antibodies.

The invention also provides an immunoconjugate comprising an antibody of the invention, or antigen-binding portion thereof, linked to a therapeutic agent, such as a radioactive isotope. The invention also provides a bispecific molecule comprising an antibody, or antigen-binding portion thereof, of the invention, linked to a second functional moiety (e.g., a second antibody) having a different binding specificity than said antibody, or antigen-binding portion thereof.

Compositions comprising an antibody, or antigen-binding portion thereof, or immunoconjugate, or bispecific molecule of the invention, and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. A method for preparing an anti-PD-1 antibody using the host cell comprising the expression vector is also provided, and comprises steps of (i) expressing the antibody in the host cell and (ii) isolating the antibody from the host cell.

In yet another aspect, the invention provides a method of modulating an immune response in a subject comprising administering to the subject the antibody, or antigen binding portion thereof, of the invention such that the immune response in the subject is modulated. Preferably, the antibody, or antigen-binding portion thereof, of the invention enhances, stimulates or increases the immune response in the subject. In a further aspect, the invention provides a method of inhibiting growth of tumor cells in a subject, comprising administering to a subject a therapeutically effective amount of the antibody, or antigen-binding portion thereof, of the present invention. In one embodiment, the tumor is a solid tumor selected from the group consisting of colon carcinoma, colorectal adenocarcinoma, lung cancer, lymphoma, mesothelioma, melanoma, or renal-cell cancer.

Still further, the invention provides a method of enhancing an immune response to an antigen in a subject, comprising administering to the subject: (i) the antigen; and (ii) an anti-PD-1 antibody, or antigen-binding portion thereof, such that an immune response to the antigen in the subject is enhanced. The antigen can be, for example, a tumor antigen, a viral antigen, a bacterial antigen or an antigen from a pathogen.

The antibodies of the invention can be used in combination with at least one additional agent such as an immunostimulatory antibody (e.g., an anti-PD-L1 antibody, an anti-TIM-3 antibody, and/or an anti-CTLA-4 antibody), a cytokine (e.g., IL-2 and/or IL-21), or a costimulatory antibody (e.g., an anti-CD137 and/or anti-GITR antibody).

Other features and advantages of the instant invention will be apparent from the following detailed description and examples which should not be construed as limiting. The contents of all references, GenBank entries, patents and published patent applications cited throughout this application are expressly incorporated herein by reference.

BRIEF DESCRIPTION OF THE DRAWINGS

FIGS. 8A and 8B show the anti-PD-1 antibody 21F12-1F6 induces human T cells to release IL2 (A) and IFNγ (B).

FIG. 9 shows the blocking capacity of the anti-PD-1 antibody 21F12-1F6-IgG1 on PD-1-PD-L1 interaction in Jurkat-NFAT-PD1 reporter gene system.

FIG. 10 shows the binding capacity of the antibody 21F12-1F6-IgG1 to FcγRI.

DETAILED DESCRIPTION OF THE INVENTION

Figure 1:
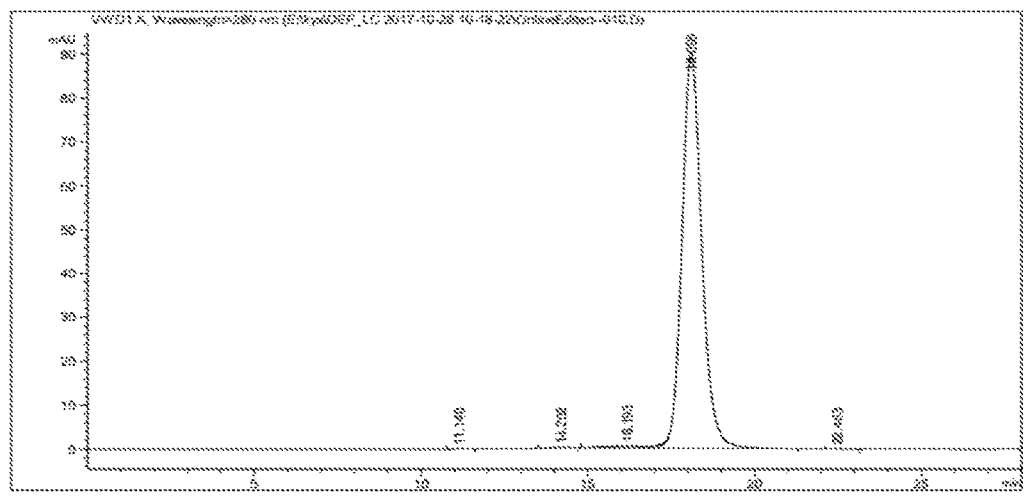
FIG. 1 shows the HPLC profile of the anti-PD-1 antibody 21F12.
Figure 2A:
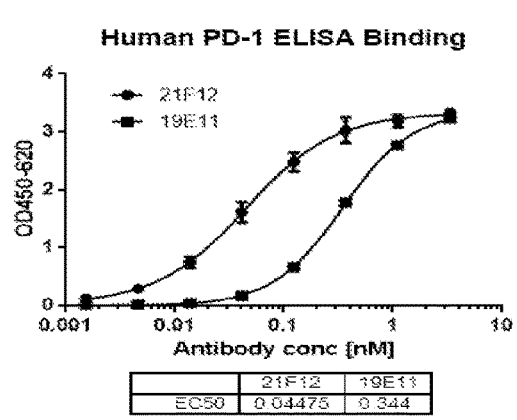
FIG. 2A to 2D show the binding capacity of the anti-PD-1 antibody 21F12, 19E11 (FIG. 2A), 21F12-1F6-IgG1, 21F12-1B12 (FIG. 2B), 21F12-1E11, 21F12-1E10, 21F12-3G1 FIG. 2C, and 21F12-1E11, 21F12-1B12, 21F12-2E1, 21F12-2H7 (FIG. 2D) to human PD-1.
Figure 2B:
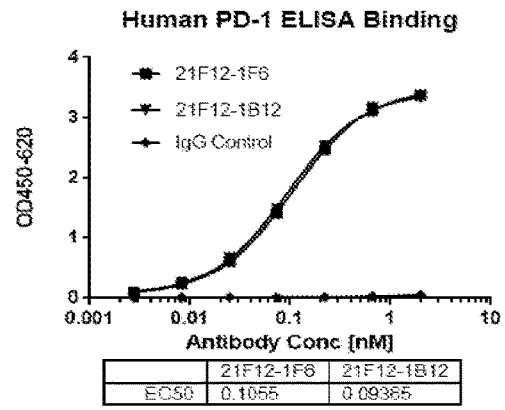
Figure 2C:
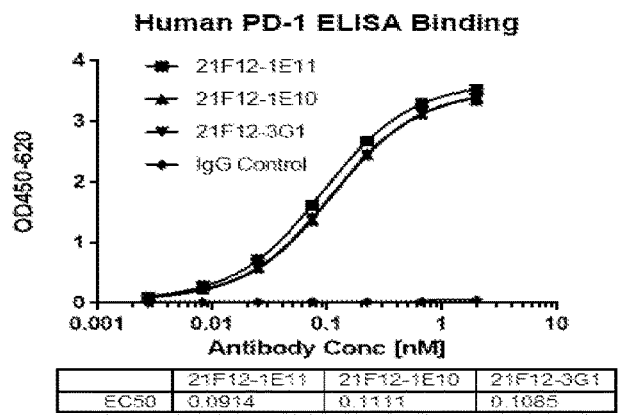
Figure 2D:
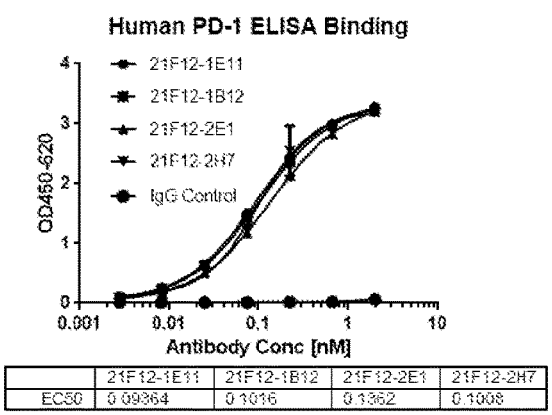

In order that the present disclosure may be more readily understood, certain terms are first defined. Additional definitions are set forth throughout the detailed description.

The term "PD-1" refers to programmed cell death protein 1. The term "PD-1" comprises variants, isoforms, homologs, orthologs and paralogs. For example, an antibody specific for a human PD-1 protein may, in certain cases, cross-reacts with a PD-1 protein from a species other than human, such as cynomolgus monkey. In other embodiments, an antibody specific for a human PD-1 protein may be completely specific for the human PD-1 protein and exhibit no cross-reactivity to other species or of other types, or may cross-react with PD-1 from certain other species but not all other species.

The term "human PD-1" refers to human sequence of PD-1, such as the complete amino acid sequence of human PD-1 having Genbank Accession No. NP_005009.2.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can normally mediate the binding of the immunoglobulin to host tissues or factors, including various cells of the immune system (e.g., effector cells) and the first component (C1q) of the classical complement system. Sometimes, the heavy chain constant region is modified to eliminate such functions.

The term "antigen-binding portion" of an antibody (or simply "antibody portion"), as used herein, refers to one or more fragments of an antibody that retain the ability to specifically bind to an antigen (e.g., a PD-1 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a PD-1 protein is substantially free of antibodies that specifically bind antigens other than PD-1 proteins). An isolated antibody that specifically binds a human PD-1 protein may, however, have cross-reactivity to other antigens, such as PD-1 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "antibody derivatives" refers to any modified form of the antibody, e.g., a conjugate of the antibody and another agent or antibody.

As used herein, an antibody that "specifically binds to human PD-1" is intended to refer to an antibody that binds to human PD-1 protein (and possibly a PD-1 protein from one or more non-human species) but does not substantially bind to non-PD-1 proteins. Preferably, the antibody binds to a human PD-1 protein with "high affinity", namely with a KD of $1\times10^{-8}$ M or less, and more preferably $5\times10^{-9}$ M or less.

The term "does not substantially bind" to a protein or cells, as used herein, means does not bind or does not bind with a high affinity to the protein or cells, i.e. binds to the protein or cells with a KD of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface plasmon resonance, preferably using a biosensor system such as a Biacore™ system.

The term "high affinity" for an IgG antibody refers to an antibody having a KD of $1\times10^{-6}$ M or less, more preferably $5\times10^{-8}$ M or less, even more preferably $1\times10^{-8}$ M or less, and even more preferably $5\times10^{-9}$ M or less for a target antigen. However, "high affinity" binding can vary for other antibody isotypes. For example, "high affinity" binding for an IgM isotype refers to an antibody having a KD of $10^{-6}$ M or less, more preferably $10^{-7}$ M or less, even more preferably $10^{-8}$ M or less.

The term "$IC_{50}$", also known as half maximal inhibitory concentration, refers to the concentration of an antibody which inhibits a specific biological or biochemical function by 50% relative to the absence of the antibody.

The term "$EC_{50}$", also known as half maximal effective concentration, refers to the concentration of an antibody which induces a response halfway between the baseline and maximum after a specified exposure time.

The term "antibody-dependent cellular cytotoxicity", "antibody-dependent cell-mediated cytotoxicity" or "ADCC," as used herein, refers to a mechanism of cell-mediated immune defense whereby an effector cell of the immune system actively lyses a target cell, such as a tumor cell, whose membrane-surface antigens have been bound by antibodies. The antibody of the invention does not induce ADCC on PD-1-expressing cells so as to protect immune cells.

The term "complement-dependent cytotoxicity" or "CDC" generally refers to an effector function of IgG and IgM antibodies, which trigger classical complement pathway when bound to a surface antigen, inducing formation of a membrane attack complex and target cell lysis. The antibody of the invention does not induce CDC on PD-1-expressing cells so as to protect immune cells.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

Various aspects of the invention are described in further detail in the following subsections.

The present invention is directed to anti-PD-1 antibodies, whose sequence information are summarized in Table 1 below.

The CDR regions in Table 1 have been determined by the Kabat numbering system. However, as is well known in the art, CDR regions can also be determined by other systems such as Chothia, CCG, and IMGT system/method, based on heavy chain/light chain variable region sequences.

TABLE 1

| Amino Acid SEQ ID NOs. of Anti-PD-1 Antibodies | | | | | | | | | | | | |
|---|---|---|---|---|---|---|---|---|---|---|---|---|
| | SEQ ID NO. | | | | | | | | | | | |
| Antibody | $V_H$ CDR1 | $V_H$ CDR2 | $V_H$ CDR3 | $V_H$ | $C_H$ | Heavy chain | $V_L$ CDR1 | $V_L$ CDR2 | $V_L$ CDR3 | $V_L$ | $C_L$ | Light chain |
| 21F12 | 1 | 2 | 3 | 8 | 18 | 21 | 5 | 6 | 7 | 17 | 20 | 39 |
| | | | | | 19 | 22 | | | | | | |
| 21F12-1B12 | 1 | 2 | 3 | 9 | 18 | 23 | 5 | 6 | 7 | 17 | 20 | 39 |
| | | | | | 19 | 24 | | | | | | |
| 21F12-1E11 | 1 | 2 | 3 | 10 | 18 | 25 | 5 | 6 | 7 | 17 | 20 | 39 |
| | | | | | 19 | 26 | | | | | | |

TABLE 1-continued

Amino Acid SEQ ID NOs. of Anti-PD-1 Antibodies

| | | | | | | SEQ ID NO. | | | | | | |
|---|---|---|---|---|---|---|---|---|---|---|---|---|
| Antibody | $V_H$ CDR1 | $V_H$ CDR2 | $V_H$ CDR3 | $V_H$ | $C_H$ | Heavy chain | $V_L$ CDR1 | $V_L$ CDR2 | $V_L$ CDR3 | $V_L$ | $C_L$ | Light chain |
| 21F12-2E1 | 1 | 2 | 3 | 11 | 18 | 27 | 5 | 6 | 7 | 17 | 20 | 39 |
| | | | | | 19 | 28 | | | | | | |
| 21F12-2H7 | 1 | 2 | 3 | 12 | 18 | 29 | 5 | 6 | 7 | 17 | 20 | 39 |
| | | | | | 19 | 30 | | | | | | |
| 21F12-1C4 | 1 | 2 | 3 | 13 | 18 | 31 | 5 | 6 | 7 | 17 | 20 | 39 |
| | | | | | 19 | 32 | | | | | | |
| 21F12-1E10 | 1 | 2 | 3 | 14 | 18 | 33 | 5 | 6 | 7 | 17 | 20 | 39 |
| | | | | | 19 | 34 | | | | | | |
| 21F12-1F6 | 1 | 2 | 3 | 15 | 18 | 35 | 5 | 6 | 7 | 17 | 20 | 39 |
| | | | | | 19 | 36 | | | | | | |
| 21F12-3G1 | 1 | 2 | 4 | 16 | 18 | 37 | 5 | 6 | 7 | 17 | 20 | 39 |
| | | | | | 19 | 38 | | | | | | |

The antibodies of the invention may contain mutant IgG1 constant region having an amino acid sequence of SEQ ID NO.:18. The antibodies of the invention may also contain IgG4 constant region having an amino acid sequence of SEQ ID NO.: 19.

Anti-PD-1 Antibodies Having Increased Binding Capacity to PD-1 and Advantageous Functional Properties The antibody, or the antigen-binding portion thereof, of the invention has comparable or even better binding affinity/capacity to human PD-1 or monkey PD-1 as compared to prior art anti-PD-1 antibodies such as Nivolumab. Further, the antibody, or the antigen-binding portion thereof, of the invention induces PBMCs to release more IL-2 and IFNγ, and provides better in vivo anti-tumor effect, than prior art anti-PD-1 antibodies such as Nivolumab.

In specific, the antibody, or the antigen-binding portion thereof, of the invention binds to human PD-1 with a $K_D$ of approximately $1.406 \times 10^{-9}$ M or less and inhibits the binding of PD-L1/PD-L2 to PD-1. The antibody, or the antigen-binding portion thereof, of the invention does not bind to mouse PD-1, and does not cross react with CD28, ICOS, BTLA or CTLA-4. Further, the antibody, or the antigen-binding portion thereof, of the invention binds to cynomolgus monkey PD-1 with a lower $EC_{50}$ value, and induces PBMCs release higher levels of IL-2 secretion and IFNγ, than prior art anti-PD-1 antibodies such as Nivolumab. The antibody, or the antigen-binding portion thereof, of the invention stimulates antigen-specific memory responses, and/or stimulates antibody responses.

Preferred antibodies of the invention are human monoclonal antibodies. Additionally or alternatively, the antibodies can be, for example, chimeric or humanized monoclonal antibodies.

Monoclonal Anti-PD-1 Antibody

The $V_H$ and $V_L$ sequences (or CDR sequences) of other anti-PD-1 antibodies which bind to human PD-1 can be "mixed and matched" with the $V_H$ and $V_L$ sequences (or CDR sequences) of the anti-PD-1 antibody of the present invention. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the invention, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another anti-PD-1 antibody, wherein the antibody specifically binds human PD-1.

In another embodiment, an antibody of the invention, or an antigen binding portion thereof, comprises:
(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-PD-1 antibody, wherein the antibody specifically binds human PD-1.

In yet another embodiment, the antibody, or antigen binding portion thereof, includes the heavy chain variable CDR2 region of anti-PD-1 antibody combined with CDRs of other antibodies which bind human PD-1, e.g., CDR1 and/or CDR3 from the heavy chain variable region, and/or CDR1, CDR2, and/or CDR3 from the light chain variable region of a different anti-PD-1 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the invention comprise the CDR2 of the heavy chain variable region of the anti-PD-1 antibody and at least the CDR3 of the heavy and/or light chain variable region of the anti-PD-1 antibody, or the CDR3 of the heavy and/or light chain variable region of another anti-PD-1 antibody, wherein the antibody is capable of specifically binding to human PD-1. These antibodies preferably (a) compete for binding with PD-1; (b) retain the functional characteristics; (c) bind to the same epitope; and/or (d) have a similar binding affinity as the anti-PD-1 antibody of the present invention. In yet another embodiment, the antibodies further may comprise the CDR2 of the light chain variable region of the anti-PD-1 antibody, or the CDR2 of the light chain variable region of another anti-PD-1 antibody, wherein the antibody is capable of specifically binding to human PD-1. In another embodiment, the antibodies of the invention may include the CDR1 of the heavy and/or light chain variable region of the anti-PD-1 antibody, or the CDR1 of the heavy and/or light chain variable region of another anti-PD-1 antibody, wherein the antibody is capable of specifically binding to human PD-1.

Conservative Modifications

In another embodiment, an antibody of the invention comprises a heavy and/or light chain variable region sequences of CDR1, CDR2 and CDR3 sequences which differ from those of the anti-PD-1 antibodies of the present invention by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.*32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:
(a) the heavy chain variable region CDR1 sequence comprises a sequence listed in Table 1 above, and/or conservative modifications thereof; and/or
(b) the heavy chain variable region CDR2 sequence comprises a sequence listed in Table 1 above, and/or conservative modifications thereof; and/or
(c) the heavy chain variable region CDR3 sequence comprises a sequence listed in Table 1 above, and conservative modifications thereof; and/or
(d) the light chain variable region CDR1, and/or CDR2, and/or CDR3 sequences comprise the sequence(s) listed in Table 1 above; and/or conservative modifications thereof; and
(e) the antibody specifically binds human PD-1.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Engineered and Modified Antibodies

Antibodies of the invention can be prepared using an antibody having one or more of the $V_H/V_L$ sequences of the anti-PD-1 antibody of the present invention as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332:323-327; Jones et al. (1986) *Nature* 321:522-525; Queen et al. (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the invention pertains to an isolated monoclonal antibody, or antigen binding portion thereof, comprising a heavy chain variable region comprising CDR1, CDR2, and CDR3 sequences comprising the sequences of the present invention, as described above, and/or a light chain variable region comprising CDR1, CDR2, and CDR3 sequences comprising the sequences of the present invention, as described above. While these antibodies contain the $V_H$ and $V_L$ CDR sequences of the monoclonal antibody of the present invention, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrccpe.cam.ac.uk/vbase), as well as in Rabat et al. (1991), cited supra; Tomlinson et al. (1992) *J. Mol. Biol.* 227:776-798; and Cox et al. (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank™ Accession Nos.: 1-69 (NG-0010109, NT-024637 & BC070333), 3-33 (NG-0010109 &NT-024637) and 3-7 (NG-0010109 & NT-024637). As another example, the following heavy chain germline sequences found in the HCol2 HuMAb mouse are available in the accompanying Genbank™ Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art.

Preferred framework sequences for use in the antibodies of the invention are those that are structurally similar to the framework sequences used by antibodies of the invention. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the invention provides isolated anti-PD-1 monoclonal antibodies, or antigen binding portions thereof, comprising a heavy chain variable region comprising: (a) a $V_H$ CDR1 region comprising the sequence of the present invention, or an amino acid sequence having one, two, three, four or five amino acid substitutions, deletions or additions; (b) a $V_H$ CDR2 region comprising the sequence of the present invention, or an amino acid sequence having one, two, three, four or five amino acid substitutions, deletions or additions; (c) a $V_H$ CDR3 region comprising the sequence of the present invention, or an amino acid sequence having one, two, three, four or five amino acid substitutions, deletions or additions; (d) a $V_L$ CDR1 region comprising the sequence of the present invention, or an amino acid sequence having one, two, three, four or five amino acid substitutions, deletions or additions; (e) a $V_L$ CDR2 region comprising the sequence of the present invention, or an amino acid sequence having one, two, three, four or five amino acid substitutions, deletions or additions; and (f) a $V_L$ CDR3 region comprising the sequence of the present invention, or an amino acid sequence having one, two, three, four or five amino acid substitutions, deletions or additions.

Engineered antibodies of the invention include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to increase the biological half-life of the antibody. More specifically, one or more amino acid mutations are introduced into the $C_{H2}$-$C_{H3}$ domain interface region of the Fc-hinge fragment such that the antibody has impaired Staphylococcal protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al. (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EPO 154 316 and EP 0 401 384.

Antibody's Physical Properties

Antibodies of the invention can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. In some instances, it is preferred to have an anti-PD-1 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-PD-1 antibody that contains a pI value that falls in the normal range. This can be achieved either by selecting antibodies with a pI in the normal range or by mutating charged surface residues.

Nucleic Acid Molecules Encoding Antibodies of the Invention

In another aspect, the invention provides nucleic acid molecules that encode heavy and/or light chain variable regions, or CDRs, of the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention include those encoding the $V_H$ and $V_L$ sequences of the PD-1 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of mouse/human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of mouse/human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA*

77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Immunoconjugates

Antibodies of the invention can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083,312; and WO 08/103,693; U.S. Patent Publications 20060024317; 20060004081; and 20060247295; the disclosures of which are incorporated herein by reference.

Bispecific Molecules

In another aspect, the present disclosure features bispecific molecules comprising one or more antibodies of the invention linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-PD-1 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry*, 9 (6), 635-644 (1998); and van Spriel et al., *Immunology Today*, 21 (8), 391-397 (2000), and the references cited therein.

Pharmaceutical Compositions

In another aspect, the present disclosure provides a pharmaceutical composition comprising one or more antibodies of the present invention formulated together with a pharmaceutically acceptable carrier. The composition may optionally contain one or more additional pharmaceutically active ingredients, such as another antibody or a drug. The pharmaceutical compositions of the invention also can be administered in a combination therapy with, for example, another immune-stimulatory agent, anti-cancer agent, an anti-viral agent, or a vaccine, such that the anti-PD-1 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

The pharmaceutical compositions of the invention can include pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-PD-1 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.*29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Invention

Antibodies (compositions, bispecifics, and immunoconjugates) of the present invention have numerous in vitro and in vivo utilities involving, for example, enhancement of immune responses by blockade of PD-1. The antibodies can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-PD-1 antibodies can be administered together with an antigen of interest or the antigen may already be present in the subject to be treated (e.g., a tumor-bearing or virus-bearing subject). When antibodies to PD-1 are administered together with another agent, the two can be administered in either order or simultaneously.

Given the ability of anti-PD-1 antibodies of the invention to inhibit the binding of PD-1 to PD-L1 and/or PD-L2 molecules and to stimulate antigen-specific T cell responses, the invention also provides in vitro and in vivo methods of using the antibodies to stimulate, enhance or upregulate antigen-specific T cell responses. For example, the invention provides a method of stimulating an antigen-specific T cell response comprising contacting said T cell with an antibody of the invention, such that an antigen-specific T cell response is stimulated. Any suitable indicator of an antigen-specific T cell response can be used to measure the antigen-specific T cell response.

Non-limiting examples of such suitable indicators include increased T cell proliferation in the presence of the antibody and/or increase cytokine production in the presence of the antibody. In a preferred embodiment, interleukin-2 production by the antigen-specific T cell is stimulated.

The invention also provides a method for stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another embodiment, the invention provides methods for inhibiting growth of tumor cells in a subject comprising administering to the subject an antibody of the invention such that growth of the tumor is inhibited in the subject. In yet another embodiment, the invention provides methods for treating a viral infection in a subject comprising administering to the subject an antibody of the invention such that the viral infection is treated in the subject.

These and other methods of the invention are discussed in further detail below.

Cancer

Blockade of PD-1 by antibodies can enhance the immune response to cancerous cells in the patient. In one aspect, the present invention relates to treatment of a subject in vivo using an anti-PD-1 antibody such that growth of cancerous tumors is inhibited. An anti-PD-1 antibody can be used alone to inhibit the growth of cancerous tumors. Alternatively, an anti-PD-1 antibody can be used in conjunction with other immunogenic agents used in cancer treatments such as oncolytic viruses, or other antibodies, as described below.

Accordingly, in one embodiment, the invention provides a method of inhibiting growth of tumor cells in a subject, comprising administering to the subject a therapeutically effective amount of an anti-PD-1 antibody, or antigen-binding portion thereof. Preferably, the antibody is a chimeric or humanized anti-PD-1 antibody.

Preferred cancers whose growth may be inhibited using the antibodies of the invention include cancers typically responsive to immunotherapy. Non-limiting examples of preferred cancers for treatment include lung cancer, lymphoma, mesothelioma, melanoma, and renal-cell cancer. Additionally, the invention includes refractory or recurrent malignancies whose growth may be inhibited using the antibodies of the invention.

Examples of other cancers that can be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) *Int. Immunol.* 17:133-144).

Optionally, antibodies to PD-1 can be combined with an immunogenic agent, such as cancerous cells, purified tumor antigens (including recombinant proteins, peptides, and carbohydrate molecules), and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

PD-1 blockade is likely to be more effective when combined with a vaccination protocol. Many experimental strategies for vaccination against tumors have been devised (see Rosenberg, S., 2000, *Development of Cancer Vaccines*, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., *Cancer Vaccines*, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-1 blockade can be used in conjunction with a collection of recombinant proteins and/or peptides expressed in a tumor in order to generate an immune response to these proteins. These proteins are normally viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). These somatic tissues may be protected from immune attack by various means. Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) Science 269:1585-1588; Tamura et al. (1997) Science 278:117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization can be effectively combined with PD-1 blockade to activate more potent anti-tumor responses.

PD-1 blockade can also be combined with standard cancer treatments. PD-1 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-PD-1 antibody in combination with decarbazine for the treatment of melanoma. Another example of such a combination is an anti-PD-1 antibody in combination with interleukin-2 (IL-2) for the treatment of melanoma. The scientific rationale behind the combined use of PD-1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors can also be combined with PD-1 blockade. Inhibition of angiogenesis leads to tumor cell death which may feed tumor antigen into host antigen presentation pathways.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-PD-1 to counteract the effects of the immunosuppressive agent and favor tumor immune responses by the host.

Other antibodies which activate host immune responsiveness can be used in combination with anti-PD-1. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with PD-1 antibodies (Ito et al. (2000) *Immunobiology* 201 (5) 527-40). Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997) *Nature Medicine* 3: 682-685 (1997), and ICOS (Hutloff et al. (1999) *Nature* 397: 262-266) may also provide for increased levels of T cell activation.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-PD-1 antibodies can increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-PD-1 antibody, or antigen-binding portion thereof, such that the subject is treated for the infectious disease. Preferably, the antibody is a chimeric, humanized or human antibody.

Similar to its application to tumors as discussed above, antibody mediated PD-1 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa.*

Combination Therapy

In another aspect, the invention provides methods of combination therapy in which an anti-PD-1 antibody (or antigen-binding portion thereof) of the present invention is co-administered with one or more additional antibodies that are effective in stimulating immune responses to thereby further enhance, stimulate or upregulate immune responses in a subject. In one embodiment, the invention provides a method for stimulating an immune response in a subject comprising administering to the subject an anti-PD-1 antibody and one or more additional immune-stimulatory antibodies, such as an anti-LAG-3 antibody, an anti-PD-L1 antibody and/or an anti-CTLA-4 antibody, such that an immune response is stimulated in the subject, for example to inhibit tumor growth or to stimulate an anti-viral response.

In another embodiment, the invention provides a method for treating a hyperproliferative disease (e.g., cancer), comprising administering to the subject an anti-PD-1 antibody and one or more additional immune-stimulatory antibodies, such as an anti-LAG-3 antibody, an anti-PD-L1 antibody and/or an anti-CTLA-4 antibody, such that the tumor growth is inhibited.

Blockade of PD-1 and one or more second target antigens such as CTLA-4 and/or LAG-3 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-PD-1 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

A combined PD-1 and CTLA-4 and/or LAG-3 and/or PD-L1 blockade can also be further combined with standard cancer treatments. For example, a combined PD-1 and CTLA-4 and/or LAG-3 and/or PD-L1 blockade can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304).

In another example, a combination of anti-PD-1 and anti-CTLA-4 and/or anti-LAG-3 antibodies and/or anti-PD-L1 antibodies can be used in conjunction with anti-neoplastic antibodies, such as Rituxan™ (rituximab), Herceptin™ (trastuzumab), Bexxar™ (tositumomab), Zevalin™ (ibritumomab), Campath™ (alemtuzumab), Lymphocide™ (epratuzumab), Avastin™ (bevacizumab), and Tarceva™ (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, LAG-3, PD-L1 or PD-1. In an exemplary embodiment, a treatment of a hyperproliferative disease (e.g., a cancer tumor) can include an anti-cancer antibody in combination with anti-PD-1 and anti-CTLA-4 and/or anti-LAG-3 and/or anti-PD-L1 antibodies, concurrently or sequentially or any combination thereof, which can potentiate anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). In another example, antibodies to each of these entities can be further combined with an anti-PD-1 and anti-CTLA-4 and/or anti-LAG-3 and/or anti-PD-L1 antibody combination to counteract the effects of immunosuppressive agents and favor anti-tumor immune responses by the host.

Other antibodies that can be used to activate host immune responsiveness can be further used in combination with an anti-PD-1 and anti-CTLA-4 and/or anti-LAG-3 and/or anti-PD-L1 antibody combination. These include molecules on the surface of dendritic cells that activate DC function and antigen presentation. Anti-CD40 antibodies (Ridge et al., supra) can be used in conjunction with an anti-PD-1 and anti-CTLA-4 and/or anti-LAG-3 and/or anti-PD-L1 combination (Ito et al., supra). Other activating antibodies to T cell costimulatory molecules (Weinberg et al., supra, Melero et al. supra, Hutloff et al., supra) may also provide for increased levels of T cell activation.

Several experimental treatment protocols involve ex vivo activation and expansion of antigen specific T cells and adoptive transfer of these cells into recipients of antigen-specific T cells against tumor (Greenberg & Riddell, supra). These methods can also be used to activate T cell responses to infectious agents such as CMV. Ex vivo activation in the presence of anti-PD-1 and anti-CTLA-4 and/or anti-LAG-3 and/or anti-PD-L1 antibodies can be expected to increase the frequency and activity of the adoptively transferred T cells.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Phage Panning, Screening and Affinity Maturation

Phage Library

An antibody single chain phage display library was created by cloning a repertoire of light chain variable regions (VL) and heavy chain variable regions (VH). The heavy and light chain repertoires were created by PCR amplification from human lymphocytes mainly collected from peripheral blood. The VL repertoire and VH repertoire were mixed and underwent PCR with overlapping primers. The final format of the antibody was a single chain Fv (scFv) with VH and VL fragments joined by a flexible linker peptide (GGGGSGGGGSGGGGS (SEQ ID NO: 60)).

Phage Library Panning Against Human PD-1

Selection of phage particles displaying specific scFv fragments was performed on Immuno 96 MicroWell™ Plates (Nunc, Denmark). First, 50 μg/ml of PD-1 recombinant protein (AcroBiosystems, cat #PD1-H5221) in phosphate-buffered saline (PBS) was coated on the plates overnight at 4° C. Following blocking with 2% (w/v) milk powder in PBS (2% MPBS), a library containing about $10^{11}$ phage particles were added and the plate was incubated for 2 hours at room temperature (RT, 25-28° C.). Non-bound phages were removed by washing plates 10-20 times with PBS containing 0.1% Tween 20 (PBS-T), followed by 10-20 times washing with PBS. The bound phages were eluted by incubation with 50 μl of 1 μg/μl trypsin for 10 min, followed by 50 μl of 50 mM glycine-HCl pH 2.0 (immediately neutralized with 50 μl of 200 mM $Na_2HPO_4$, pH7.5 after 10 min). Four rounds of panning were performed.

Phage Screening

From the third and fourth round of panning, phages were picked up and tested for human PD-1 binding. In specific, human PD-1 (AcroBiosystems, cat #PD1-H5221) were coated on 96-well plates at 0.1 μg/mL, and single clone phages were added into plates. Then, unbounded phages were washed away and bound phages were detected by anti-M13 secondary antibody (Abcam, cat #ab50370).

ELISA positive clones were sequenced, from which 5 unique sequences were identified, including clone 21F12, 16B2, 16C1, 19E11 and 45E2. The amino acid sequence ID numbers of the heavy/light chain variable regions of the anti-PD-1 antibody 21F12 were shown in Table 1 above.

Affinity Maturation

To improve the binding affinity of antibodies from clone 21F12, two phage libraries for HCDR1 and HCDR3 were constructed for panning. After 3 rounds of panning, variants were tested for positive binding to human PD-1 (AcroBiosystems, cat #PD1-H5221) by ELISA screening. Off-rate ranking of positive variants was determined by Octet Red 96 (Fortebio). Clones with improved off-rate were picked and converted to full length IgG for analysis. The amino acid sequence ID numbers of the heavy/light chain of the variant anti-PD-1 antibodies 21F12-1B12, 21F12-1E11, 21F12-

2E1, 21F12-2H7, 21F12-1C4, 21F12-1E10, 21F12-1F6-IgG1, and 21F12-3G1 were also summarized in Table 1 above.

Nucleotide sequences encoding the heavy chain and light chain of each anti-PD-1 antibody were inserted into the expression vector pcDNA3.1 (Invitrogen), wherein the antibodies contained a mutant IgG1 constant region having an amino acid sequence set forth in SEQ ID NO.: 18 and an light chain constant region having an amino acid sequence set forth in SEQ ID NO.: 20. Vectors were co-transfected into CHO—S cells using ExpiCHO™ Expression System (ThermoFisher) according to the manufacturer's instructions. The transfected cells were cultured in ExpiCHO™ Expression Medium for 12 days, and then culture supernatants were harvested and sent for purification with Protein A affinity chromatography (GE healthcare).

Example 2 Physical and Chemical Characteristics of Anti-PD-1 Monoclonal Antibody Antibodies from clone 21F12 were tested in Size Exclusion Chromatography. In particular, 20 μg of sample was injected on a TSK G3000SWXL column using 100 mM sodium phosphate+100 mM $Na_2SO_4$, pH 7.0, as running buffer. The run time was 29 min. All measurements were performed on Agilent 1220 HPLC. Data was analyzed using OpenLAB software.

As shown in FIG. 1, the main peak of the antibody 21F12 was above 95% in SEC, suggesting high purity and integrity of the purified antibody.

Example 3 Anti-PD-1 Antibodies Bound to Human PD-1

An ELISA assay was performed for determination of the relative binding capacity of the antibodies to human PD-1. Human PD-1 protein (SINO Biological Inc., Cat #10377-H08H-100) was immobilized onto 96-well plates by incubation overnight at 4° C., 25 ng/well. The plates were then blocked by incubation with 1% BSA in PBS for one hour at 37° C. After blocking, the plates were washed three times with PBST (PBS containing 0.05% Tween20). Serially diluted anti-PD-1 antibodies (with mutant IgG1 constant region of SEQ ID NO.: 18) or human IgG control (prepared according to US20190016800A1, using the heavy and light chain amino acid sequences set forth in SEQ ID NOs: 61 and 62) were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled Goat anti-human F(ab')2 antibody (Jackson Immuno Research, Cat #109-035-097) diluted 1/20,000 in binding buffer, washed again, developed with TMB (ThermoFisher Cat #34028) for 15 minutes, and then stopped with 1M $H_2SO_4$. Each plate well contained 50 μL of solution at each step.

The absorbance at 450 nm-620 nm was determined. The $EC_{50}$ values and binding curves for the antibodies binding to human PD-1 were shown in FIG. 2A to 2D, suggesting the anti-PD-1 antibodies of the invention specifically bound to human PD-1.

Example 4 Anti-PD-1 Antibodies Bound to Human and Cynomolgus PD-1

An ELISA assay was performed for determination of the relative binding activity of antibodies to recombinant human, cynomolgus and mouse PD-1.

Human PD-1 protein (SINO Biological Inc., Cat #10377-H08H-100), cynomolgus PD-1 protein (Acrobiosystems, Cat #PD1-05223), or mouse PD-1 protein (SINO Biological Inc., Cat #50124-M08H) was immobilized onto 96-well plates by incubation overnight at 4° C., 25 ng/well. The plates were then blocked by incubation with 1% BSA in PBS for one hour at 37° C. After blocking, the plates were washed three times with PBST (PBS containing 0.05% Tween20). Serially diluted Nivolumab analog (used as the positive control, prepared using the heavy and light chain amino acid sequences set forth in SEQ ID NOs: 63 and 64), anti-PD-1 antibodies 21F12-1F6-IgG1 (with the mutant IgG1 constant region of SEQ ID NO.:18), human IgG control (as prepared in Example 3) were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled Goat anti-human F(ab')2 antibody (Jackson Immuno Research, Cat #109-035-097) diluted 1/20,000 in binding buffer, washed again, developed with TMB (ThermoFisher Cat #34028) for 15 minutes, and then stopped with 1M $H_2SO_4$. Each plate well contained 50 μL of solution at each step.

Figure 3A:
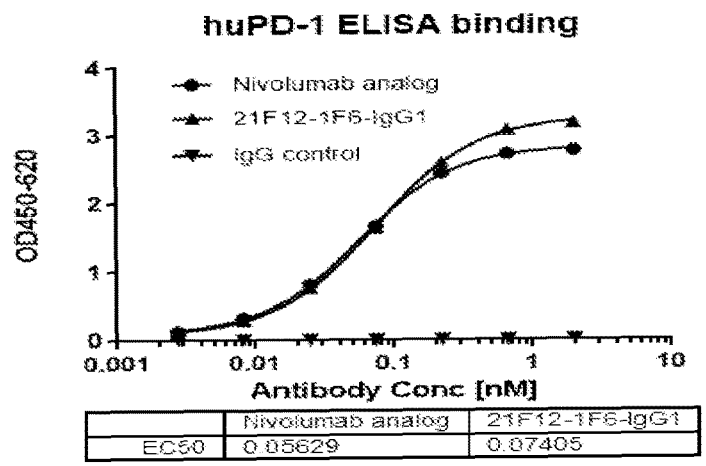
FIG. 3A to 3C show the binding capacity of the anti-PD-1 antibody 21F12-1F6-IgG1 to human PD-1 (FIG. 3A), cynomolgus monkey PD-1 (FIG. 3B) and mouse PD-1 (FIG. 3C).
Figure 3B:
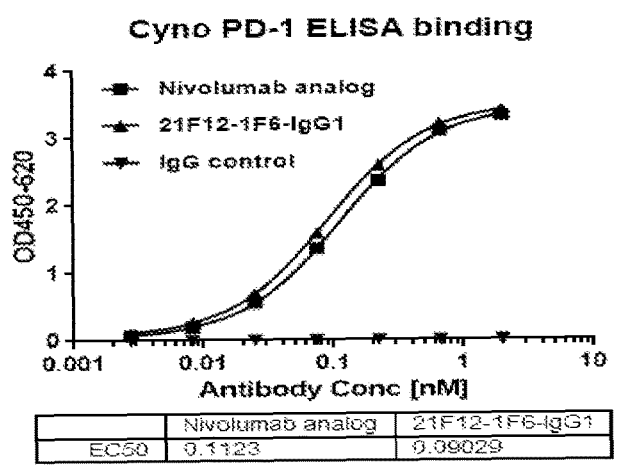
Figure 3C:
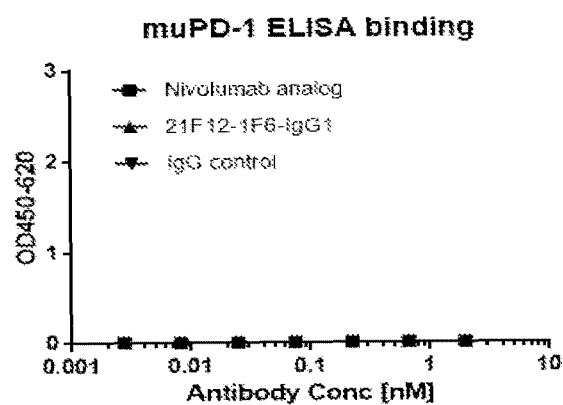
Figure 4A:
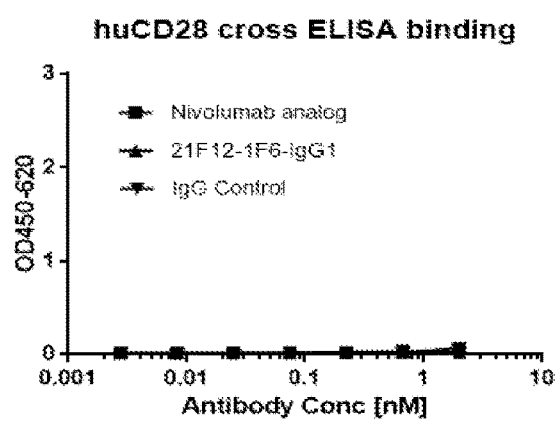
FIG. 4A to 4D show the cross reactivity of the anti-PD-1 antibody 21F12-1F6-IgG1 to human CD28 (FIG. 4A), human ICOS (FIG. 4B), human BTLA (FIG. 4C) and human CTLA4 (FIG. 4D).
Figure 4B:
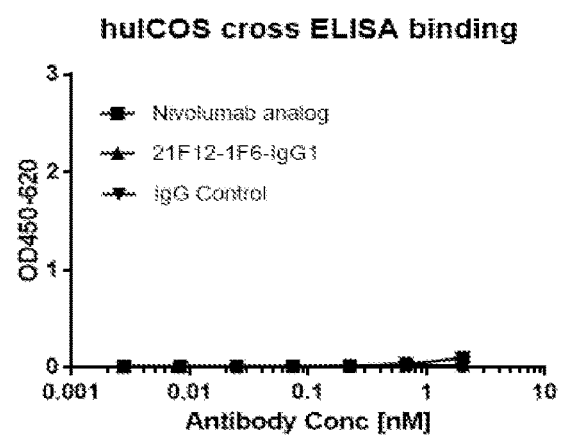
Figure 4C:
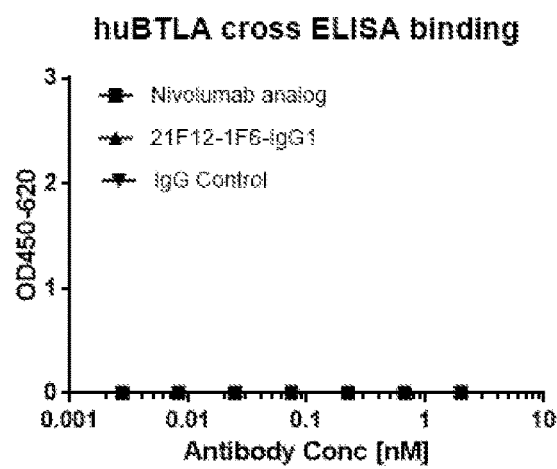
Figure 4D:
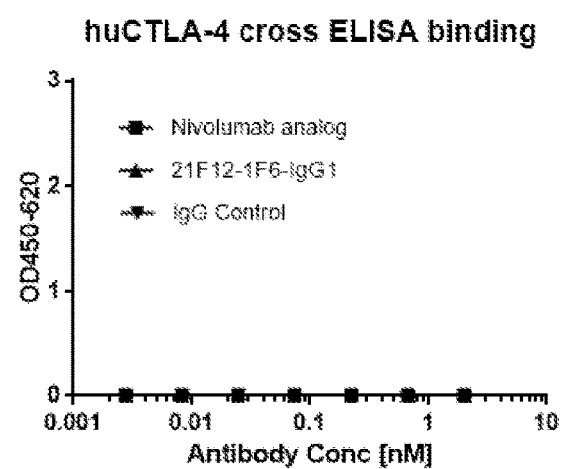

The absorbance at 450 nm-620 nm was determined. The $EC_{50}$ values and binding curves for the antibodies binding to human PD-1, cynomolgus PD-1 or mouse PD-1 were shown in FIG. 3A to 3C. The data suggested that the anti-PD-1 antibody 21F12-1F6-IgG1 bound to human and monkey PD-1 specifically but did not bind to mouse PD-1. Especially, the antibody 21F12-1F6-IgG1 bound to monkey PD-1 with a lower $EC_{50}$ value as compared to the Nivolumab analog.

Example 5 Binding Affinity of Anti-PD-1 Antibody to Human and Cynomolgus PD-1 Protein The kinetic binding activity of the antibody 21F12-1F6 to human PD-1 and cynomolgus PD-1 was measured by surface plasmon resonance (SPR) using a Biacore™ X100 system (Biacore, GE Healthcare).

In brief, 50 pg/mL Goat anti-human Fcy (Jackson Immuno Catalog #109-005-098) in immobilization buffer (10 mM Sodium Acetate, pH4.5) was injected into flow cell, resulting in immobilization levels of 8008.5 RU. The anti-PD-1 antibody 21F12-1F6 (with the mutant IgGI constant region of SEQ ID NO.: 18) with running buffer (HBS-EP+ buffer) were injected at a flow rate of 5 pL/min into the flow cell. Varying concentrations of human PD-1-his protein (Acrobiosystems, Cat #PDI-H5221), ranging from 12.5 nM to 200 nM, were prepared with dilution in running buffer. The human PD-1 protein of each concentration was injected at a flow rate of 30 pL/min for an association phase of 120 s, followed by 500 s dissociation. Following each cycle, the CM5 chip surface was regenerated with injection of 10 mM GlycineHCl (pH1.5) at a flow rate of 30 pL/min for 30 s. Background subtraction binding sensorgrams were used for analyzing the rate of association Ka and dissociation Kd, and the equilibrium dissociation constant $K_D$ was calculated accordingly. The resulting data sets were fitted with a 1:1 *Langmuir* Binding Model using the Biacore™ X100 evaluation software.

For monkey PD-1 binding, 50 pg/mL Goat anti-human Fcy (Jackson Immuno Catalog #109-005-098) in immobilization buffer (10 mM Sodium Acetate, pH4.5) was injected into flow cell, resulting in immobilization level of 7807.1 RU. The anti-PD-1 antibody 21F12-1F6 with running buffer (HBS-EP+ buffer) were injected at a flow rate of 5 pL/min into the flow cell. Varying concentrations of cynomolgus PD-1-his protein (Acrobiosystems, Cat #PDI-05223), ranging from 12.5 nM to 200 nM, were prepared with dilution in running buffer. Cynomolgus PD-1 protein at each concentration was injected to the flow cell at a flow rate of 30 pL/min for an association phase of 120 s, followed by 500 s dissociation. Following each cycle, the CM5 chip surface was regenerated with injection of 10 mM Glycine-HCl (pH1.5) at a flow rate of 30 pL/min for 30 s. Background subtraction binding sensorgrams were used for analyzing the rate of association Ka and dissociation Kd, and the equilibrium dissociation constant $K_D$ was calculated accordingly. The resulting data sets were fitted with a 1:1 Langmuir Binding Model using the Biacore™ X100 evaluation software Table 2 below summarized the binding affinity of the anti-PD-1 antibody 21F12-1F6-IgG1 to human PD-1 protein and cynomolgus PD-1 protein.

TABLE 2

Binding affinity of anti-PD-1 antibody to human PD-1 protein and cynomolgus PD-1 proteins

| Antibody | PD-1 protein | $K_a(M^{-1}S^{-1})$ | $K_d(S^{-1})$ | $K_D(M)$ |
|---|---|---|---|---|
| 21F12-1F6-IgG1 | huPD-1-his | 6.476E+5 | 9.106E-5 | 1.406E-9 |
|  | cynoPD-1-his | 9.672E+4 | 1.096E-4 | 1.133E-9 |

Example 6 Anti-PD-1 Antibody Did not Cross React with Human ICOS, Human CD28, Human CTLA-4 or Human BTLA An ELISA assay was used for determination of the binding activity of the anti-PD-1 antibodies to recombinant human ICOS, human CD28, human CTLA4 and human BTLA.

Human ICOS (Acrobiosystems, Cat #ICS-H5250), human CD28 (Acrobiosystems, Cat #11524-H02H), human CTLA-4 (Acrobiosystems, Cat #CT4-H5229), or human BTLA (Acrobiosystems, Cat #BTA-H52E0) was immobilized onto 96-well plates by incubation overnight at 4° C., 25 ng/well. The plates were then blocked by incubation with 1% BSA in PBS for one hour at 37° C. After blocking, the plates were washed three times with PBST (PBS containing 0.05% Tween20). Serially diluted Nivolumab analog (as prepared in Example 4), 21F12-1F6-IgG1 (with the mutant IgG1 constant region of SEQ ID NO.: 18), and human IgG control (as prepared in Example 3) were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled Goat anti-human F(ab')2 antibody (Jackson Immuno Research, Cat #109-035-097) diluted 1/20,000 in binding buffer, washed again, developed with TMB (ThermoFisher Cat #34028) for 15 minutes, and then stopped with 1M $H_2SO_4$. Each plate well contained 50 μL of solution at each step.

The absorbance at 450 nm-620 nm was determined. The representative binding curves of the antibodies binding to human ICOS, human CD28, human CTLA4 and human BTLA were shown in FIG. 4A to 4D, respectively. The data showed that the anti-PD-1 antibody 21F12-1F6-IgG1 did not bind to the proteins as tested.

Example 7 Anti-PD1 Antibodies Blocked Interaction of PD-1 with PD-L1 or PD-L2

To assess the ability of the anti-PD-1 antibodies to inhibit human PD-1 binding to human PD-L1 or PD-L2, an ELISA blocking assay was performed.

Human PD-1 (prepared in Leadsbiolabs, amino acid sequence of NP_005009.2 set forth in SEQ ID NO.: 66) was immobilized onto 96-well plates by incubation overnight at 4° C., 25 ng/well. Nonspecific binding sites were blocked by incubation with 1% BSA in PBS for one hour at 37° C. After blocking, the plates were washed three times with PBST (PBS containing 0.05% Tween20). Serially diluted Nivolumab analog (as prepared in Example 4), anti-PD-121F12 antibodies (all with the mutant IgG1 constant region of SEQ ID NO.: 18), and human IgG control (as prepared in Example 3) were prepared in binding buffer (PBS containing 0.05% Tween20 and 0.5% BSA) and mixed with Human PD-L1-mouse Fc-tag (prepared in Leadsbiolabs, amino acid sequence set forth in SEQ ID NO.: 65) that had been prepared at 0.8 m/mL at the same volume, then the obtained mixtures were incubated with the immobilized proteins for one hour at 37° C. After that, the plates were washed three times with PBST, incubated for one hour at 37° C. with peroxidase-labeled Goat anti mouse-Fc IgG (Jackson Immuno Research, cat #115-035-164) diluted 1/10,000 in binding buffer, washed again, developed with TMB (ThermoFisher Cat #34028) for 15 minutes, and then stopped with 1M $H_2SO_4$. Each plate well contained 50 μL of solution at each step.

The absorbance at 450 nm-620 nm was determined. Representative binding curves and $IC_{50}$ values for these antibodies were shown in FIG. 5A to 5E. The result indicated that the anti-PD-1 antibodies of the invention blocked interaction between human PD1 and PD-L1.

Similarly, 100 ng/well human PD-1 (prepared in Leadsbiolabs, amino acid sequence set forth in SEQ ID NO.: 66) was immobilized onto 96-well plates by incubation overnight at 4° C. Nonspecific binding sites were blocked by incubation with 1% BSA in PBS for one hour at 37° C. After blocking, the plates were washed three times with PBST (PBS containing 0.05% Tween20). Serially diluted Nivolumab analog (as prepared in Example 4), 21F12-1F6-IgG1 (with the mutant IgG1 constant region of SEQ ID NO.:18), and human IgG control (as prepared in Example 3) were prepared in binding buffer (PBS containing 0.05% Tween20 and 0.5% BSA) and mixed with Human PD-L2-his-tag (SINO Biological Inc, Cat #10292-H08H) that had been prepared at 0.8 m/mL at the same volume, then the obtained mixtures were incubated with the immobilized proteins for one hour at 37° C. After that, the plates were washed three times with PBST, incubated for one hour at 37° C. with peroxidase-labeled mouse anti his-tag antibody (GenScript, Cat #A00612) diluted 1/5,000 in binding buffer, washed again, developed with TMB (ThermoFisher Cat #34028) for 15 minutes, and then stopped with 1M $H_2SO_4$. Each plate well contained 50 μL of solution at each step.

Figure 5A:
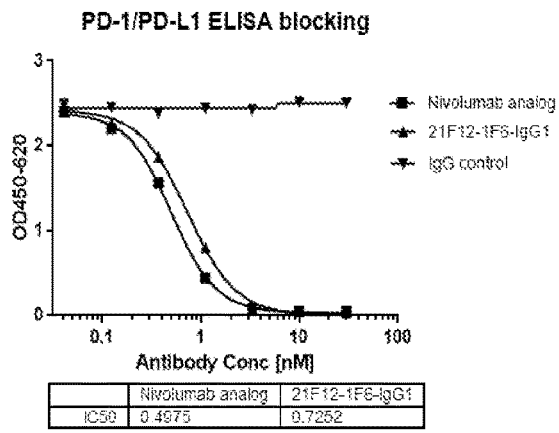
FIG. 5A to 5F show the blocking capacity of the anti-PD-1 antibody 21F12-1F6-IgG1 (FIG. 5A), 21F12, 21F12-3G1 (FIG. 5B), 21F12, 21F12-1E11, 21F12-1B12, 21F12-2E1, 21F12-2H7 (FIG. 5C), 21F12-1C4, 21F12 (FIG. 5D), and 21F12-1E10, 21F12 (FIG. 5E) on human PD-1/PD-L1 interaction, and the blocking capacity of the anti-PD-1 antibody 21F12-1F6-IgG1 on human PD-1/PD-L2 interaction (FIG. 5F).
Figure 5B:
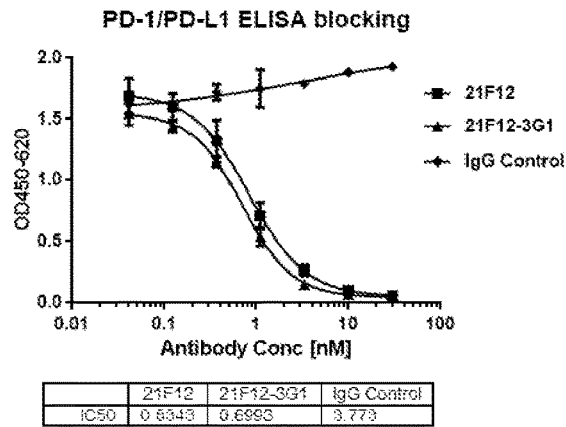
Figure 5C:
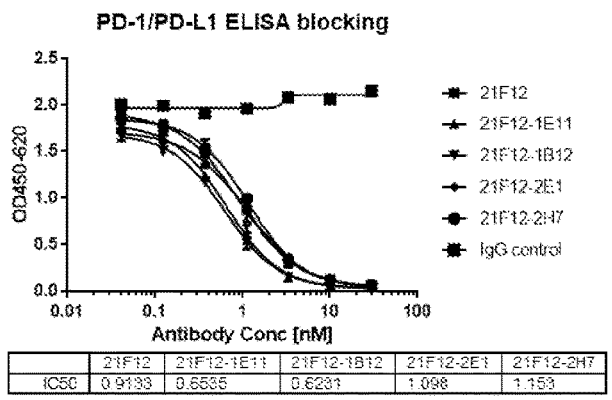
Figure 5D:
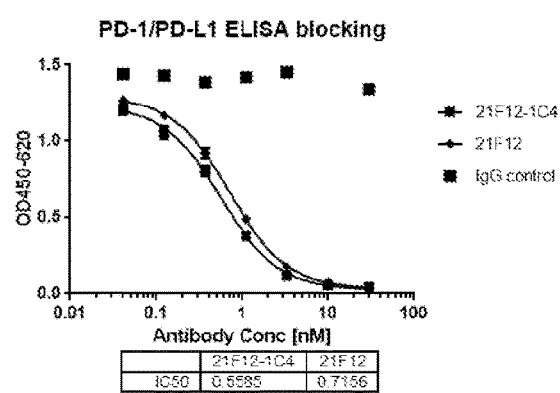
Figure 5E:
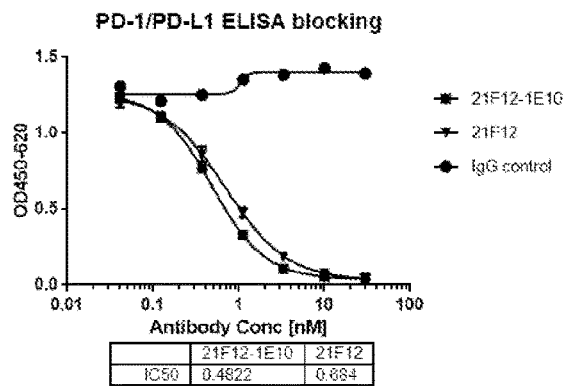
Figure 5F:
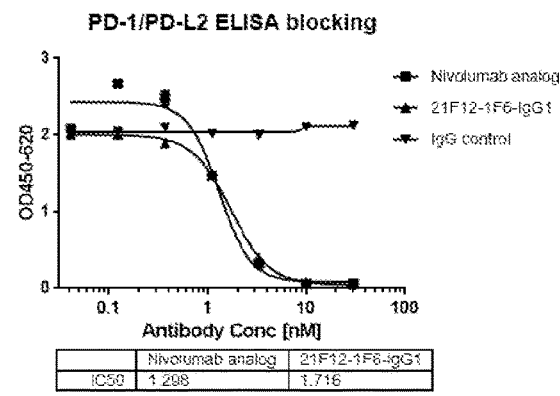

The absorbance at 450 nm-620 nm was determined. Representative binding curves and $IC_{50}$ values for these antibodies were shown in FIG. 5F. The result indicated the antibody 21F12-1F6-IgG1 blocked interaction between human PD-1 and PD-L2.

Example 8 Anti PD-1 Antibodies Bound to Cell Surface PD-1 Expressed by CHO-K1-PD-1 Cells Anti-PD-1 antibodies were tested for their ability of binding to human PD-1 stably expressed on CHO-K1 cells.

A Chinese hamster ovary epithelial CHO-K1 cell line (ATCC, cat #CCL-61) was maintained in F-12K medium containing 10% FBS in a humidified incubator with 5% $CO_2$ at 37° C. Nucleic acid sequences encoding human PD-1 of SEQ ID NO.: 66 were transfected to CHO-K1 cells using Polyethylenimine (MW25K, 23966-2, Polyscience), and a clone stably expressing human PD-1 was obtained by limited dilution.

Figure 6A:
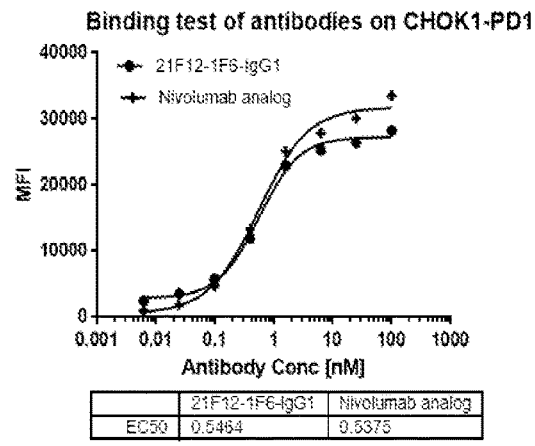
FIGS. 6A and 6B show the binding capacity of the anti-PD-1 antibody 21F12-1F6-IgG1 (FIG. 6A), 21F12, 21F12-1C4, 21F12-1E10, 21F12-1B12 and 21F12-3G1 (FIG. 6B) to PD-1 expressed on CHO-K1-PD-1 cells.
Figure 6B:
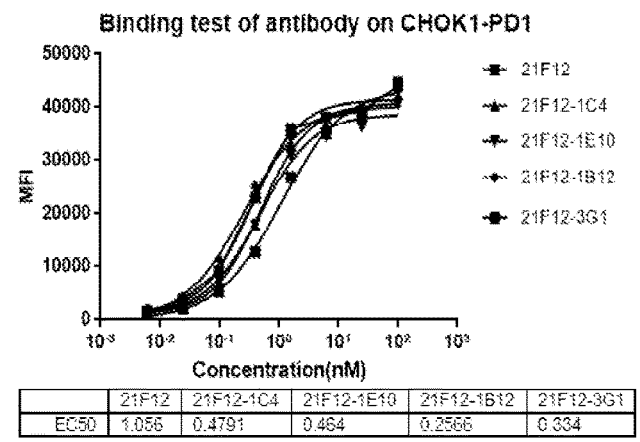

Serially diluted anti-PD-1 antibodies were added to 50 μL of 10000 CHO-K1 cells prepared above. The obtained mixtures were incubated at 4° C. for 30 min, then the cells were washed twice by PBS buffer. The binding was detected using a PE-labeled donkey anti-human IgG (Jackson Immuno Research Cat #109-116-098) secondary reagent in PBS buffer (1:100) by incubating the secondary reagent with the mixtures at 4° C. for 30 min followed by washing twice. After that, cells were resuspended in PBS buffer. Analysis of human PD-1 binding was carried out with the BD Accuri C5 flow cytometer (BD Bioscience). Representative binding curves and $EC_{50}$ values for these antibodies were shown in FIGS. 6A and 6B.

The result indicated that anti-PD-1 antibodies of the invention (with the mutant IgG1 constant region of SEQ ID NO.: 18) and the Nivolumab analog, bound to human PD-1 stably expressed on CHO-K1 cells specifically, with similar $EC_{50}$ values.

Example 9 Anti PD-1 Antibodies Bound to Cell Surface PD-1 Expressed by Stimulated PBMCs Anti-PD-1 antibodies were tested for their ability of binding to human and cynomolgus PD-1 expressed on stimulated PBMCs.

Figure 7A:
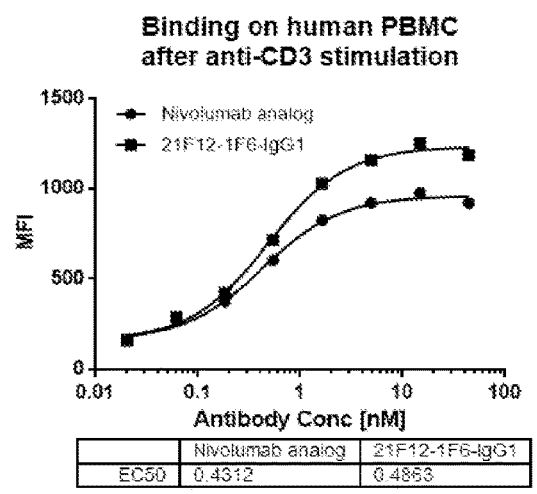
FIGS. 7A and 7B show the binding capacity of the anti-PD-1 antibody 21F12-1F6-IgG1 to PD-1 expressed on human PBMCs (FIG. 7A) or cynomolgus monkey PBMCs (FIG. 7B).
Figure 7B:
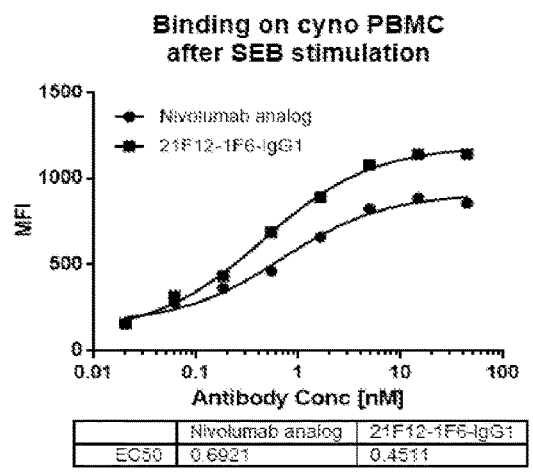

Human and cynomolgus PBMCs were isolated from peripheral blood by density gradient centrifugation. $3*10^6$ human PBMCs were pre-stimulated by coated anti-CD3 (Biogems, cat #05121-25-500) antibody for 24 hours at concentration of 5 μg/mL diluted in PBS (Hyclone, cat #SH3025601). $3*10^6$ cynomolgus PBMCs were pre-stimulated by SEB (Toxin Tech, cat #BT202) at concentration of 20 ng/mL for 2 days. Serially diluted Nivolumab analog (as prepared in Example 4) and 21F12-1F6-IgG1 (with the mutant IgG1 constant region of SEQ ID NO.: 18) were added to 100,000 human PBMCs or 100,000 cynomolgus PBMCs, respectively. The mixtures were incubated at 4° C. for 30 minutes, and then the cells were washed twice using PBS (Hyclone, cat #SH3025601) buffer. The cells were incubated with a PE-labeled goat anti-human IgG (Jackson Immuno Research, cat #109-116-098) secondary reagent according to the manufacturer's instructions at 4° C. for 30 minutes, and then washed twice. After that, cells were resuspended in PBS buffer. Analysis of PD-1 binding was carried out with the BD Accuri C5 flow cytometer (BD Bioscience). Representative binding curves and $EC_{50}$ values for these antibodies were shown in FIGS. 7A and 7B.

The result indicated that anti-PD-1 antibodies, both 21F12-1F6-IgG1 and the Nivolumab analog, can specifically bind to PD-1 expressed on human and cynomolgus stimulated PBMCs, wherein the antibody 21F12-1F6-IgG1 bound to monkey PD-1 with a lower $EC_{50}$ value as compared to the Nivolumab analog.

Example 10 Anti-PD-1 Antibodies Induced Human T Cells to Release IL-2 and IFNγ

The functional activity of the anti-PD-1 antibodies was assessed on human PBMCs after SEB stimulation.

Human PBMCs were isolated from peripheral blood of healthy donors by density gradient centrifugation. Heparinized blood was diluted by two fold volume PBS, and the diluted blood were layered in SepMate™-50 (Stemcell, cat #86450) tubes. After centrifugation at 1200 g for 10 mins at room temperature, the lymphocyte containing fractions were harvested and washed with PBS, resuspended in freezing medium composed with 10% DMSO (Sigma, cat #D2650) and 90% FBS (Gibco, cat #10099141), and then stored in liquid nitrogen. $7.5*10^6$ human PBMCs were stimulated with SEB (Toxin Tech, cat #BT202) at the concentration of 20 ng/mL for 24 hours. 100,000 obtained cells were plated in each well of a 96-well plate in complete RPMI 1640 (Gibco, cat #22400089). Serially diluted Nivolumab analog (as prepared in Example 4), 21F12-1F6 (with the mutant IgG1 constant region of SEQ ID NO.:18), and human IgG control (Biolegend, Cat #QA16A15) were added into the medium, respectively. SEB was added at a final concentration of 20 ng/mL, and the obtained mixture was incubated at 37° C. for 2 days, and culture supernatants were collected and the IL-2 and IFNγ level were detected by ELISA using Human IL2 ELISA kit (R&D, cat #DY202) and Human IFN-gamma ELISA kit (R&D, cat #DY285B) according to the manufacturer's instructions.

The IL-2 levels were shown in FIG. 8A, while the IFNγ levels were shown in FIG. 8B.

The result indicated that stimulated human PBMCs released higher levels of IL2 and IFNγ with 21F12-1F6 treatment compared treatment of Nivolumab analog or IgG control.

Example 11 Anti-PD-1 Antibodies Induced Jurkat-NFAT-PD1 Report Gene Luminescence The activity of the anti-PD-1 antibodies was assessed on Jurkat-NFAT-PD-1 report gene assay.

When Jurkat-NFAT-PD1 effector cells were co-cultured with CHO-PDL1/CD3 target cells, the TCR-NFAT mediated luminescence was inhibited for PD-1-PD-L1 interaction. After adding to the cell mixture the anti-PD-1 antibodies, the PD-1-PDL1 interaction was blocked and luminescence was then recovered.

A Chinese hamster ovary epithelial CHO-K1 cell line (ATCC, cat #CCL-61) was maintained in F-12K medium containing 10% FBS in a humidified incubator with 5% $CO_2$ at 37° C. Nucleic acid sequences encoding human PD-L1 (amino acid of NP_054862.1 as set forth in SEQ ID NO.:67) and OKT3-scFv (amino acid sequence set forth in SEQ ID NO.:68) were co-transfected to CHO-K1 cells using Polyethylenimine (MW25K, 23966-2, Polyscience), and a clone stably expressing human PD-L1 and OKT3-scFv was obtained by limited dilution. The obtained CHO-PDL1/CD3 target cells were plated on the 96 well plate (30000 cells/well) on day 1. On day 2, the medium (DMEM-F12 containing 10% FBS) on the 96 well plate was discarded, and then serially diluted anti-PD-1 antibodies and Jurkat-NFAT-PD1 cells (prepared by co-transfecting a Jurkat cell line (CBTCCCAS, Clone E6-1) with nucleic acid sequences encoding human PD-1 of SEQ ID NO.:66 and pGL4.30 [luc2P/NFAT-RE/Hygro] (Promega, E848A) by electroporation, a clone stably expressing human PD-1 and NFAT was obtained by limited dilution) (30000 cells/well) were added to the plate. The plate was incubated in a 37° C., 5% $CO_2$ incubator for six hours. Then 60 μL of One-Glo™ Reagent (Promega Corporation Cat #E6130) was added to the wells of the assay plates and luminescence was measured using a luminescence plate reader (Tecan F200). The $EC_{50}$ values were calculated, and representative curves for blocking the PD-L1 and PD-1 interaction were shown in FIG. 9.

The result indicated the anti-PD-1 antibody 21F12-1F6-IgG1 (with the mutant IgG1 constant region of SEQ ID NO.:

18) and the Nivolumab analog blocked interaction between human PD-1 and PD-L1 with similar $EC_{50}$ values.

Example 12 FcγRI Binding

The mutant IgG1 constant region with L234A, L235A, D265A and P329A mutations or IgG4 constant region was used as the heavy chain constant region of the antibody 21F12-1F6-IgG1 to eliminate the FcγR-Fc interaction. An ELISA assay was used for determination of the relative binding activity of the obtained antibodies to human FcγRIs.

Human FcγRI (Acrobiosystems, Cat #FCA-H52H2) was immobilized onto 96-well plates by incubation overnight at 4° C. The plates were then blocked by incubation with 1% BSA in PBS for one hour at 37° C., 200 µL/well. After blocking, the plates were washed three times with PBST (PBS containing 0.05% Tween20). Serially diluted Rituximab analog (used as the positive control, prepared according to U.S. Pat. No. 5,736,137, with the heavy and light chain amino acid sequences set forth in SEQ ID NOs: 69 and 70), 21F12-1F6-IgG1 with the mutant IgG1 constant region and 21F12-1F6-IgG1 with IgG4 constant region were prepared in binding buffer (PBS containing 0.05% Tween20 and 0.5% BSA) and incubated with the immobilized proteins for one hour at 37° C. After binding, the plates were washed three times with PBST, incubated for one hour at 37° C. with peroxidase-labeled Goat anti-human F(ab')2 antibody (Jackson Immuno Research, Cat: 109-035-097) diluted 1/10,000 in binding buffer, washed again, developed with TMB (ThermoFisher Cat #34028) for 15 minutes, and then stopped with 1M $H_2SO_4$. Each plate well contained 50 µL of solution at each step, unless otherwise indicated.

The absorbance at 450 nm-620 nm was determined. The $EC_{50}$ and representative binding curves for the FcγRI-antibody binding were shown in FIG. 10.

The result indicated 21F12-1F6-IgG1 having IgG4 heavy chain constant region or mutant IgG1 heavy chain constant region bound to Human FcγRI very weakly as compared to the Rituximab analog having wild type IgG1 heavy chain constant region.

Example 13 Anti-PD-1 Antibodies Did not Induce Antibody-Dependent Cell-Mediated Cytotoxicity (ADCC)

Antibody-Dependent Cell-Mediated Cytotoxicity (ADCC) assay was performed on Jurkat-PD1 cells. The Jurkat-PD-1 cells were prepared by transfecting a Jurkat cell line (CBTCCCAS, Clone E6-1) with the nucleic acid sequence encoding human PD-1 (amino acid set forth in SEQ ID NO.:66) by electroporation. A clone stably expressing human PD-1 was obtained by limited dilution.

Jurkat-PD1 cells were seeded at a density of 10,000 cells per well and were pre-incubated with 100 nM or 10 nM anti-PD-1 antibodies (with the mutant IgG1 constant region or IgG4 constant region) in assay buffer (Phenol red free MEM medium+1% FBS) for 30 min. PBMC effector cells from healthy donors were added to initiate the ADCC effects at E/T ratios at 10:1, 25:1 or 50:1. The ADCC effect of the Rituximab analog (as prepared in Example 13) on Daudi (CBTCCCAS, cat #TCHu140) was used as an internal control to assure the assay quality. After incubation in a 37° C., 5% $CO_2$ incubator for 24 hours, cell supernatants were then collected for measuring released LDH using a cytotoxicity LDH assay kit (Dojindo, Cat #CK12). Absorbance at $OD_{490nm}$ was read on F50 (Tecan). The percentages of cell lysis were calculated according the formula below, % Cell lysis=100×($OD_{sample}$−$OD_{target\ cells\ plus\ effector\ cells}$)/($OD_{Maximum\ release}$−$OD_{Minimum\ release}$).

Data was analyzed by Graphpad Prism.

The data showed that neither anti-PD-1 antibody 21F12-1F6-IgG1 having the mutant IgG1 constant region nor 21F12-1F6-IgG1 having the IgG4 constant region had ADCC activity on Jurkat-PD1 cells.

Example 14 Anti-PD-1 Antibodies Did not Induce Complement-Dependent Cytotoxicity (CDC)

Complement-Dependent Cytotoxicity (CDC) assay on Jurkat-PD1 cells. Jurkat-PD1 cells were seeded at a density of 5,000 cells per well and were pre-incubated with 100 nM or 10 nM antibodies in assay buffer (Phenol red free MEM medium+1% FBS) for 30 min. The plates were then added with plasma from healthy donors at the concentration of 10 vol %, 20 vol % and 50 vol % to initiate the CDC effects. After incubation in a 37° C., 5% $CO_2$ incubator for 4 hours, cells were added with Cell-Titer Glo reagent (Promega, Cat #G7572) and the RLU data was read on F200 (Tecan). The percentages of cell lysis were calculated according the formula below, % Cell lysis=100×(1−($RLU_{sample}$)/($RLU_{cell+NHP}$)) in which NHP represented normal human plasma.

The data showed that neither anti-PD-1 antibody 21F12-1F6-IgG1 having the mutant IgG1 constant region nor 21F12-1F6-IgG1 having the IgG4 constant region had CDC activity on Jurkat-PD1 cells.

Example 15 Anti-PD-1 Antibodies had In Vivo Anti-Tumor Effect

The in vivo efficacy of the anti-PD-1 antibodies was studied in hPD-1 KI mice bearing colon carcinoma.

For the experiments herein, humanized mice C57BL/6J-Pdcd1$^{em1(PDCD1)Smoc}$ expressing the extracellular portion of human PD-1 were purchased from Shanghai Model Organisms Center, Inc.

MC38 murine colon carcinoma cell line was purchased from Obio Technology (Shanghai) Corp., Ltd. MC38 cells were transduced with nucleic acid sequence encoding ovalbumin (OVA) (amino acid of AAB59956 as set forth in SEQ ID NO.: 71) using retroviral transduction. The cells were subsequently cloned by limiting dilution. The clones highly expressing OVA protein were selected using an ELISA kit (cloud clone corp, CEB459Ge). The MC38-OVA clones were maintained in complete media with 10% fetal bovine serum with 4 µg/mL Puromycin (Gibco, A11138-03).

C57BL/6J-Pdcd1$^{em1(PDCD1)Smoc}$ mice were subcutaneously implanted with 1×10$^6$ MC38-OVA cells, and were randomized on Day 0 into 3 groups (N=7 in each group) when the mean tumor volumes reached approximately 80 mm$^3$ (L×W$^2$/2). On Day 0, 3, 7, 10, and 14, mice were intraperitoneally administered with 21F12-1F6-IgG1 (with mutant IgG1 constant region, 10 mg/kg), Nivolumab analog (as prepared in Example 4, 10 mg/kg), and PBS, respectively. Tumor volumes were monitored by caliper measurement twice per week during the experiment.

Treatment of anti-PD-1 antibody 21F12-1F6-IgG1 and Nivolumab analog resulted in significant tumor growth inhibition compared to PBS group, and the 21F12-1F6-IgG1 group showed higher TGI rate compared to Nivolumab analog group (89.95% vs. 76.71%) as shown in Table 3 below.

TABLE 3

MC38-OVA tumor growth inhibition

| Group | Dose | Animal number | Tumor volume (mm³)[a] (on Day 14) | TGI (%)[b] | P[c] |
|---|---|---|---|---|---|
| PBS | / | 7 | 722.01 ± 82.28 | / | / |
| Nivolumab analog | 10 mg/kg | 7 | 163.60 ± 54.66 | 76.71% | <0.001 |
| 21F12-1F6 | 10 mg/kg | 7 | 73.73 ± 20.55 | 89.95% | <0.001 |

[a]Tumor volume data were presented as Mean ± SEM;
[b]TGI = (1 − rumor volume change in administration group/tumor volume change in control group)*100%
[c]Compared to PBS group, two-way ANOVA performed, followed by Tukey's multiple comparison test.

Sequences in the present application are summarized below.

```
Description/Sequence/SEQ ID NO.

VH-CDR1 for 21F12, 21F12-1B12, 21F12-1E11, 21F12-2E1, 21F12-2H7, 21F12-1C4, 21F12-1E10,
21F12-1F6, and 21F12-3G1
SYYIH (SEQ ID NO: 1)
AGCTACTACATCCAC (SEQ ID NO: 40)

VH-CDR2 for 21F12, 21F12-1B12, 21F12-1E11, 21F12-2E1, 21F12-2H7, 21F12-1C4, 21F12-1E10,
21F12-1F6, and 21F12-3G1
VINPSGGSTTYAQKFQG (SEQ ID NO: 2)
GTGATTAACCCCTCCGGCGGCTCCACCACCTATGCTCAGAAGTTCCAGGGC (SEQ ID NO: 41)

VH-CDR3 for 21F12, 21F12-1B12, 21F12-1E11, 21F12-2E1, 21F12-2H7, 21F12-1C4, 21F12-1E10,
21F12-1F6
GSYSSGWDYYYYYGMDV (SEQ ID NO: 3)
GGCTCCTACTCCTCCGGCTGGGATTACTACTATTACTACGGCATGGACGTG (SEQ ID NO: 42)

VH-CDR3 for 21F12-3G1
GSYNSGWDYYYYYGMDV (SEQ ID NO: 4)
GGCTCCTACAACTCCGGCTGGGATTACTACTATTACTACGGCATGGACGTG (SEQ ID NO: 43)

VL-CDR1 for 21F12, 21F12-1B12, 21F12-1E11, 21F12-2E1, 21F12-2H7, 21F12-1C4, 21F12-1E10,
21F12-1F6, and 21F12-3G1
RSSQSLLHSQGYNYLD (SEQ ID NO: 5)
CGCTCCAGCCAGTCCCTGCTGCACAGCCAGGGCTACAATTATCTGGAT (SEQ ID NO: 53)

VL-CDR2 for 21F12, 21F12-1B12, 21F12-1E11, 21F12-2E1, 21F12-2H7, 21F12-1C4, 21F12-1E10,
21F12-1F6, and 21F12-3G1
LGSNRAS (SEQ ID NO: 6)
CTGGGCTCTAACAGGGCCTCC (SEQ ID NO: 54)

VL-CDR3 for 21F12, 21F12-1B12, 21F12-1E11, 21F12-2E1, 21F12-2H7, 21F12-1C4, 21F12-1E10,
21F12-1F6, and 21F12-3G1
MQALQTPWT (SEQ ID NO: 7)
ATGCAGGCTCTGCAGACCCCATGGACA (SEQ ID NO: 55)

VH for 21F12
QMQLVQSGAEVKKPGASVKLSCKASGYIFTSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSS (SEQ ID NO: 8)
CAGATGCAGCTGGTGCAGTCCGGCGCCGAGGTGAAGAAGCCTGGCGCTTCCGTGAAGCTGTCCT
GTAAGGCCTCCGGCTACATCTTCACCAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 44)

VH for 21F12-1B12
QMQLVQSGAEVKKPGASVKLSCKASGYPFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSS (SEQ ID NO: 9)
CAGATGCAGCTGGTGCAGTCCGGCGCCGAGGTGAAGAAGCCTGGCGCTTCCGTGAAGCTGTCCT
GTAAGGCCTCCGGCTACCCCTTCCAGAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 45)
```

| Description/Sequence/SEQ ID NO. |
|---|

VH for 21F12-1E11
QMQLVQSGAEVKKPGASVKLSCKASGYFFQSYYIHWVRQAPGQGLEWVGVINPSGGSTTYAQKFQG
RVTMTRDTSISTAYMELSRLRSDDTVVYYCARGSYSSGWDYYYYGMDVWGKGTLVTVSS (SEQ ID NO: 10)
CAGATGCAGCTGGTGCAGTCCGGCGCCGAGGTGAAGAAGCCTGGCGCTTCCGTGAAGCTGTCCT
GTAAGGCCTCCGGCTACTTCTTCCAGAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 46)

VH for 21F12-2E1
QMQLVQSGAEVKKPGASVKLSCKASEYIFQSYYIHWVRQAPGQGLEWVGVINPSGGSTTYAQKFQG
RVTMTRDTSISTAYMELSRLRSDDTVVYYCARGSYSSGWDYYYYGMDVWGKGTLVTVSS (SEQ ID NO: 11)
CAGATGCAGCTGGTGCAGTCCGGCGCCGAGGTGAAGAAGCCTGGCGCTTCCGTGAAGCTGTCCT
GTAAGGCCTCCGAGTACATCTTCCAGAGCTACTACATCCACTGGGTGAGGCAGGCTCCCGGACAG
GGACTGGAATGGGTGGGCGTGATTAACCCCTCCGGCGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 47)

VH for 21F12-2H7
QMQLVQSGAEVKKPGASVKLSCKASQYIFQSYYIHWVRQAPGQGLEWVGVINPSGGSTTYAQKFQG
RVTMTRDTSISTAYMELSRLRSDDTVVYYCARGSYSSGWDYYYYGMDVWGKGTLVTVSS (SEQ ID NO: 12)
CAGATGCAGCTGGTGCAGTCCGGCGCCGAGGTGAAGAAGCCTGGCGCTTCCGTGAAGCTGTCCT
GTAAGGCCTCCCAGTACATCTTCCAGAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 48)

VH for 21F12-1C4
QMQLVQSGAEVKKPGASVKLSCKASDYIFTSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSS (SEQ ID NO: 13)
CAGATGCAGCTGGTGCAGTCCGGCGCCGAGGTGAAGAAGCCTGGCGCTTCCGTGAAGCTGTCCT
GTAAGGCCTCCGACTACATCTTCACCAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 49)

VH for 21F12-1E10
QMQLVQSGAEVKKPGASVKLSCKASGYPFTSYYIFIWVRQAPGQGLEWVGVINPSGGSTTYAQKFQG
RVTMTRDTSISTAYMELSRLRSDDTVVYYCARGSYSSGWDYYYYGMDVWGKGTLVTVSS (SEQ ID NO: 14)
CAGATGCAGCTGGTGCAGTCCGGCGCCGAGGTGAAGAAGCCTGGCGCTTCCGTGAAGCTGTCCT
GTAAGGCCTCCGGCTACCCTTTCACCAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 50)

VH for 21F12-1F6
QMQLVQSGAEVKKPGASVKLSCKASGYIFQSYYIHWVRQAPGQGLEWVGVINPSGGSTTYAQKFQG
RVTMTRDTSISTAYMELSRLRSDDTVVYYCARGSYSSGWDYYYYGMDVWGKGTLVTVSS (SEQ ID NO: 15)
CAGATGCAGCTGGTGCAGTCCGGCGCCGAGGTGAAGAAGCCTGGCGCTTCCGTGAAGCTGTCCT
GTAAGGCCTCCGGCTACATCTTCCAGAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACTCCTCCGGCTGGGATTACTA
CTATTACTACGGCATGGACGTGTGGGGCAAGGGCACCCTGGTGACCGTGAGCTCC (SEQ ID NO: 51)

VH for 21F12-3G1
QMQLVQSGAEVKKPGASVKLSCKASGYIFTSYYIHWVRQAPGQGLEWVGVINPSGGSTTYAQKFQG
RVTMTRDTSISTAYMELSRLRSDDTVVYYCARGSYNSGWDYYYYGMDVWGKGTLVTVSS (SEQ ID NO: 16)
CAGATGCAGCTGGTGCAGTCCGGCGCCGAGGTGAAGAAGCCTGGCGCTTCCGTGAAGCTGTCCT
GTAAGGCCTCCGGCTACATCTTCACCAGCTACTACATCCACTGGGTGAGGCAGGCTCCCGGACAG
GGACTGGAATGGGTGGGCGTGATTAACCCCTCCGGCGGCTCCACCACCTATGCTCAGAAGTTCCA
GGGCAGGGTGACCATGACCAGGGACACCTCCATCTCCACCGCCTACATGGAGCTGTCCAGGCTG
AGGTCCGACGACACCGTGGTGTACTACTGCGCTAGGGGCTCCTACAACTCCGGCTGGGATTACTA
CTATTACTACGGCATGGACGTGTGGGGCAAGGGCACCCTGGTGACCGTGAGCTCC (SEQ ID NO: 52)

VL for 21F12, 21F12-1B12, 21F12-1E11, 21F12-2E1, 21F12-2H7, 21F12-1C4, 21F12-1E10,
21F12-1F6, and 21F12-3G1
DVVMTQSPLSLPVTPGEPASISCRSSQSLLHSQGYNYLDWYLQKPGQSPQLLIYLGSNRASGVPDRFSG
SGSGTDFTLKISRVEAEDVGVYYCMQALQTPWTFGQGTKVEIK (SEQ ID NO: 17)
GACGTGGTCATGACCCAGAGCCCACTGTCTCTGCCAGTGACACCTGGAGAGCCAGCTTCTATCTC
CTGCCGCTCCAGCCAGTCCCTGCTGCACAGCCAGGGCTACAATTATCTGGATTGGTACCTGCAGA
AGCCCGGCCAGTCCCCTCAGCTGCTGATCTATCTGGGCTCTAACAGGGCCTCCGGAGTGCCTGAC

| Description/Sequence/SEQ ID NO. |
|---|

```
CGGTTTAGCGGCTCTGGCTCCGGCACCGATTTCACACTGAAGATCTCCAGGGTGGAGGCTGAGGA
CGTGGGCGTGTACTATTGTATGCAGGCTCTGCAGACCCCATGGACATTTGGCCAGGGCACAAAGG
TGGAGATCAAG (SEQ ID NO: 56)
```

CH for 21F12, 21F12-1B12, 21F12-1E11, 21F12-2E1, 21F12-2H7, 21F12-1C4, 21F12-1E10,
21F12-1F6, and 21F12-3G1
mutant IgG1CH
```
ASTKGPSVFPLAPSSKSTSGGTAALGCLVKDYFPEPVTVSWNSGALTSGVHTFPAVLQSSGLYSLSSV
VTVPSSSLGTQTYICNVNIIKPSNTKVDKKVEPKSCDKTHTCPPCPAPEAAGGPSVFLFPPKPKDTLMIS
RTPEVTCVVVAVSHEDPEVKFNWYVDGVEVHNAKTKPREEQYNSTYRVVSVLTVLHQDWLNGKEY
KCKVSNKALAAPIEKTISKAKGQPREPQVYTLPPSRDELTKNQVSLTCLVKGFYPSDIAVEWESNGQP
ENNYKTTPPVLDSGSFFLYSKLTVDKSRWQQGNVFSCSVMHEALHNHYTQKSLSLSPGK (SEQ ID NO: 18)
GCTAGCACCAAGGGACCATCCGTGTTCCCACTGGCCCCCTCCAGCAAGTCCACCAGCGGAGGAA
CAGCCGCTCTGGGATGCCTGGTGAAGGACTACTTCCCAGAGCCCGTGACAGTGAGCTGGAACTCT
GGCGCCCTGACCAGCGGAGTGCACACATTTCCCGCCGTGCTCCAGTCTTCCGGCCTGTACTCTCTG
AGCTCTGTGGTGACCGTGCCCTCCAGCTCTCTGGGCACCCAGACATATATCTGCAACGTGAATCA
CAAGCCAAGCAATACAAAGGTGGACAAGAAGGTGGAGCCCAAGTCTTGTGATAAGACCCATACA
TGCCCCCCTTGTCCTGCTCAGAGGCTGCTGGAGGACCAAGCGTGTTCCTGTTTCCACCCAAGCCT
AAGGACACCCTGATGATCTCCAGGACCCCCGAGGTGACATGCGTGGTGGTGGCTGTGAGCCACG
AGGACCCCGAGGTGAAGTTTAACTGGTACGTGGATGGCGTGGAGGTGCATAATGCTAAGACCAA
GCCTAGGGAGGAGCAGTACAACTCTACCTATCGGGTGGTGTCCGTGCTGACAGTGCTGCACCAGG
ACTGGCTGAACGGCAAGGAGTATAAGTGCAAGGTGTCTAATAAGGCCCTGGCTGCTCCTATCGA
GAAGACCATCTCCAAGGCCAAGGGCCAGCCTAGAGAGCCACAGGTGTACACACTGCCTCCATCT
CGCGACGAGCTGACCAAGAACCAGGTGTCCCTGACATGTCTGGTGAAGGGCTTCTATCCTTCCGA
CATCGCTGTGGAGTGGGAGAGCAACGGCCAGCCAGAGAACAATTACAAGACCACACCCCCTGTG
CTGGACTCCGATGGCAGCTTCTTTCTGTATAGCAAGCTGACCGTGGATAAGTCCAGGTGGCAGCA
GGGCAACGTGTTTTCTTGCTCCGTGATGCATGAGGCTCTGCACAATCATTATACACAGAAGAGCC
TGTCTCTGTCCCCTGGCAAGTGA (SEQ ID NO: 57)
```
IgG4CH:
```
ASTKGPSVFPLAPCSRSTSESTAALGCLVKDYFPEPVTVSWNSGALTSGVHTFPAVLQSSGLYSLSSVV
TVPSSSLGTKTYTCNVINIKPSNTKVDKRVESKYGPPCPPCPAPEFLGGPSVFLFPPKPKDTLMISRTPE
VTCVVVDVSQEDPEVQFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPSDIAVEWESNGQPENNY
KTTPPVLDSDGSFFLYSRLTVDKSRWQEGNVFSCSVMHEALHNHYTQKSLSLSLGK (SEQ ID NO: 19)
GCTAGCACAAAGGGACCTTCCGTGTTCCCACTGGCCCCCTGCTCCAGAAGCACATCTGAGTCCAC
CGCCGCTCTGGGCTGTCTGGTGAAGGACTACTTCCCTGAGCCAGTGACCGTGTCCTGGAACAGCG
GCGCCCTGACATCCGGAGTGCACACCTTTCCCGCCGTGCTCCAGTCCAGCGGACTGTACAGCCTG
TCTTCCGTGGTGACAGTGCCCAGCTCTTCCCTGGGCACCAAGACATATACCTGCAACGTGGACCA
TAAGCCTAGCAATACCAAGGTGGATAAGAGGGTGGAGTCTAAGTACGGACCACCTTGCCCACCA
TGTCCAGCTCCTGAGTTTCTGGGAGGACCATCCGTGTTCCTGTTTCCTCCAAAGCCTAAGGACACC
CTGATGATCTCTCGGACACCTGAGGTGACCTGCGTGGTGGTGGACGTGTCTCCAGGAGGACCCCGA
GGTGCAGTTCAACTGGTACGTGGATGGCGTGGAGGTGCACAATGCTAAGACCAAGCCAAGAGAG
GAGCAGTTTAATAGCACATACCGCGTGGTGTCTGTGCTGACCGTGCTGCATCAGGATTGGCTGAA
CGGCAAGGAGTATAAGTGCAAGGTGAGCAATAAGGGCCTGCCCAGCTCTATCGAAGACAATC
TCTAAGGCTAAGGGACAGCCTCGCGAGCCACAGGTGTACACCTGCCCCCTTCCCAGGAGGAGA
TGACAAAGAACCAGGTGAGCCTGACCTGTCTGGTGAAGGGCTTCTATCCATCTGACATCGCTGTG
GAGTGGGAGTCCAACGGCCAGCCCGAGAACAATTACAAGACCACACCACCCGTGCTGGACTCTG
ATGGCTCCTTCTTTCTGTATTCCAGGCTGACAGTGGATAAGAGCCGGTGGCAGGAGGGCAACGTG
TTTAGCTGCTCTGTGATGCACGAGGCTCTGCACAATCATTATACCCAGAAGTCCCTGAGCCTGTCT
CTGGGCAAGTAA (SEQ ID NO: 58)
```

CL for 21F12, 21F12-1B12, 21F12-1E11, 21F12-2E1, 21F12-2H7, 21F12-1C4, 21F12-1E10,
21F12-1F6, and 21F12-3G1
```
RTVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC (SEQ ID NO: 20)
CGTACGGTGGCTGCACCATCTGTCTTCATCTTCCCGCCATCTGATGAGCAGTTGAAATCTGGAACT
GCCTCTGTTGTGTGCCTGCTGAATAACTTCTACCCCAGAGAAGCCAAAGTGCAGTGGAAGGTGGA
CAACGCCCTGCAGAGCGGAAACAGCCAGGAAAGCGTGACAGAGCAGGATTCCAAGGATTCCACA
TACAGCCTGAGCAGCACACTGACACTGTCCAAGGCCGACTACGAGAAGCACAAGGTGTACGCCT
GCGAAGTGACACACCAGGGACTGTCCTCCCCTGTGACAAAGAGCTTCAACAGAGGAGAATGCTG
A (SEQ ID NO: 59)
```

Heavy chain for 21F12
```
QMQLVQSGAEVKKPGASVKLSCKASGYIFTSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 21)
QMQLVQSGAEVKKPGASVKLSCKASGYIFTSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 22)
```

| Description/Sequence/SEQ ID NO. |
| --- |

Heavy chain for 21F12-1B12
QMQLVQSGAEVKKPGASVKLSCKASGYPFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 23)
QMQLVQSGAEVKKPGASVKLSCKASGYPFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 24)

Heavy chain for 21F12-1E11
QMQLVQSGAEVKKPGASVKLSCKASGYFFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 25)
QMQLVQSGAEVKKPGASVKLSCKASGYFFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 26)

Heavy chain for 21F12-2E1
QMQLVQSGAEVKKPGASVKLSCKASEYIFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 27)
QMQLVQSGAEVKKPGASVKLSCKASEYIFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 28)

Heavy chain for 21F12-2H7
QMQLVQSGAEVKKPGASVKLSCKASQYIFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 29)
QMQLVQSGAEVKKPGASVKLSCKASQYIFQSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 30)

Heavy chain for 21F12-1C4
QMQLVQSGAEVKKPGASVKLSCKASDYIFTSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 31)
QMQLVQSGAEVKKPGASVKLSCKASDYIFTSYYIHWVRQAPGQGLEWVGVINPSGGSTTYAQKFQG
RVTMTRDTSISTAYMELSRLRSDDTVVYYCARGSYSSGWDYYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV

| Description/Sequence/SEQ ID NO. |
|---|

VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 32)

Heavy chain for 21F12-1E10
QMQLVQSGAEVKKPGASVKLSCKASGYPFTSYYIFIWVRQAPGQGLEWVGVINPSGGSTTYAQKFQG
RVTMTRDTSISTAYMELSRLRSDDTVVYYCARGSYSSGWDYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 33)
QMQLVQSGAEVKKPGASVKLSCKASGYPFTSYYIFIWVRQAPGQGLEWVGVINPSGGSTTYAQKFQG
RVTMTRDTSISTAYMELSRLRSDDTVVYYCARGSYSSGWDYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 34)

Heavy chain for 21F12-1F6
QMQLVQSGAEVKKPGASVKLSCKASGYIFQSYYIHWVRQAPGQGLEWVGVINPSGGSTTYAQKFQG
RVTMTRDTSISTAYMELSRLRSDDTVVYYCARGSYSSGWDYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 35)
QMQLVQSGAEVKKPGASVKLSCKASGYIFQSYYIHWVRQAPGQGLEWVGVINPSGGSTTYAQKFQG
RVTMTRDTSISTAYMELSRLRSDDTVVYYCARGSYSSGWDYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 36)

Heavy chain for 21F12-3G1
QMQLVQSGAEVKKPGASVKLSCKASGYIFTSYYIHWVRQAPGQGLEWVGVINPSGGSTTYAQKFQG
RVTMTRDTSISTAYMELSRLRSDDTVVYYCARGSYNSGWDYYYYGMDVWGKGTLVTVSSASTKG
PSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPEAAGGPSVFLFPPKPKDTLMISRTPEVT
CVVVAVSHEDPEVKFNWYVDGVEVHNAKTKPREEQYNSTYRVVSVLTVLHQDWLNGKEYKCKVS
NKALAAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO: 37)
QMQLVQSGAEVKKPGASVKLSCKASGYIFTSYYIHWVRQAPGQGLEWVGVINPSGGSTTYAQKFQG
RVTMTRDTSISTAYMELSRLRSDDTVVYYCARGSYNSGWDYYYYGMDVWGKGTLVTVSSASTKG
PSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK (SEQ ID NO: 38)

Light chain for 21F12, 21F12-1B12, 21F12-1E11, 21F12-2E1, 21F12-2H7, 21F12-1C4,
21F12-1E10, 21F12-1F6, and 21F12-3G1
DVVMTQSPLSLPVTPGEPASISCRSSQSLLHSQGYNYLDWYLQKPGQSPQLLIYLGSNRASGVPDRFSG
SGSGTDFTLKISRVEAEDVGVYYCMQALQTPWTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC (SEQ ID NO: 39)

Linker
GGGGSGGGGSGGGGS (SEQ ID NO: 60)

Heavy chain for human IgG control
QVQLQESGGGVVRPGGSLRLSCAASGFTFDDYGMSWVRQAPGKGLEWVSGINWSGGSTYYADSVK
GRSTISRDNSKNTLYLQMNSLRAEDTAVYYCATGGYWGQGTLVTVSSASTKGPSVFPLAPCSRSTSES
TAALGCLVKDYFPEPVTVSWNSGALTSGVHTFPAVLQSSGLYSLSSVVTVPSSSLGTKTYTCNVDHKP
SNTKVDKRVESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK (SEQ ID NO: 61)

Light chain for human IgG control
DIRLTQSPSSLSASVGDRVTITCRASQSISSYLNWYQQKPGKAPKLLIYAASSLQGGVPSRFSGSGSGTD
FTLTISSLQPEDSATYYC QQSYSTPYTFGQGTKLTVLGRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVT
KSFNRGEC (SEQ ID NO: 62)

-continued

| Description/Sequence/SEQ ID NO. |
|---|

Heavy chain for Nivolumab analog
QVQLVESGGGVVQPGRSLRLDCKASGITFSNSGMHWVRQAPGKGLEWVAVIWYDGSKRYYADSVK
GRFTISRDNSKNTLFLQMNSLRAEDTAVYYCATNDDYWGQGTLVTVSSASTKGPSVFPLAPCSRSTSE
STAALGCLVKDYFPEPVTVSWNSGALTSGVHTFPAVLQSSGLYSLSSVVTVPSSSLGTKTYTCNVDHK
PSNTKVDKRVESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK (SEQ ID NO: 63)

Light chain for Nivolumab analog
EIVLTQSPATLSLSPGERATLSCRASQSVSSYLAWYQQKPGQAPRLLIYDASNRATGIPARFSGSGSGT
DFTLTISSLEPEDFAVYYCQQSSNWPRTFGQGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVT
KSFNRGEC (SEQ ID NO: 64)

Human PD-L1-mouse Fc-tag
MRIFAVFIFMTYWHLLNAFTVTVPKDLYVVEYGSNMTIECKFPVEKQLDLAALIVYWEMEDKNIIQF
VHGEEDLLWQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERVPRDCGCKPCICTVPEVSSVFIFPPKPKDVLTITLT
PKVTCVVVDISKDDPEVQFSWFVDDVEVHTAQTQPREEQFNSTFRSVSELPIMHQDWLNGKEFKCRV
NSAAFPAPIEKTISKTKGRPKAPQVYTIPPPKEQMAKDKVSLTCMITDFFPEDITVEWQWNGQPAENY
KNTQPIMDTDGSYFVYSKLNVQKSNWEAGNTFTCSVLHEGLHNHHTEKSLSHSPGK (SEQ ID NO: 65)

Human PD-1
MQIPQAPWPWWAVLQLGWRPGWFLDSPDRPWNPPTFSPALLVVTEGDNATFTCSFSNTSESFVLNW
YRMSPSNQTDKLAAFPEDRSQPGQDCRFLVTQLPNGRDFHMSVVRARRNDSGTYLCGAISLAPKAQI
KESLRAELRVTERRAEVPTAHPSPSPRPAGQFQTLVVGVVGGLLGSLVLLVWVLAVICSRAARGTIGA
RRTGQPLKEDPSAVPVFSVDYGELDFQWREKTPEPPVPCVPEQTEYATIVFPSGMGTSSPARRGSADG
PRSAQPLRPEDGHCSWPL (SEQ ID NO: 66)

Human PD-L1
MRIFAVFIFMTYWHLLNAFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISYGGADYKRITVKVNAP
YNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERTHLVILGAILLCLGVALTFIFRLRKGRMMDVKKC
GIQDTNSKKQSDTHLEET (SEQ ID NO: 67)

OKT3-scFv
MERHWIFLLLLSVTAGVHSQVQLQQSGAELARPGASVKMSCKASGYTFTRYTMHWVKQRPGQGLE
WIGYINPSRGYTNYNQKFKDKATLTTDKSSSTAYMQLSSLTSEDSAVYYCARYYDDHYCLDYWGQG
TTLTVSSGGGGSGGGGSGGGGSQIVLTQSPAIMSASPGEKVTMTCSASSSVSYMNWYQQKSGTSPKR
WIYDTSKLASGVPAHFRGSGSGTSYSLTISGMEAEDAATYYCQQWSSNPFTFGSGTKLEINSSVVPVL
QKVNSTTTKPVLRTPSPVHPTGTSQPQRPEDCRPRGSVKGTGLDFACDIYIWAPLAGICVALLLSLIITLI
CYHRSRKRVCKCPRPLVRQEGKPRPSEKIV (SEQ ID NO: 68)

Heavy chain for Rituximab analog
QVQLQQPGAELVKPGASVKMSCKASGYTFTSYNMHWVKQTPGRGLEWIGAIYPGNGDTSYNQKFK
GKATLTADKSSSTAYMQLSSLTSEDSAVYYCARSTYYGGDWYFNVWGAGTTVTVSAASTKGPSVFP
LAPSSKSTSGGTAALGCLVKDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK (SEQ ID NO: 69)

Light chain for Rituximab analog
QIVLSQSPAILSASPGEKVTMTCRASSSVSYIHWFQQKPGSSPKPWIYATSNLASGVPVRFSGSGSGTSY
SLTISRVEAEDAATYYCQQWTSNPPTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTK
SFNRGEC (SEQ ID NO: 70)

Ovalbumin
MGSIGAASMEFCFDVFKELKVHHANENIFYCPIAIMSALAMVYLGAKDSTRTQINKVVRFDKLPGFG
DSIEAQCGTSVNVHSSLRDILNQITKPNDVYSFSLASRLYAEERYPILPEYLQCVKELYRGGLEPINFQT
AADQARELINSWVESQTNGIIRNVLQPSSVDSQTAMVLVNAIVFKGLWEKAFKDEDTQAMPFRVTEQ
ESKPVQMMYQIGLFRVASMASEKMKILELPFASGTMSMLVLLPDEVSGLEQLESIINFEKLTEWTSSN
VMEERKIKVYLPRMKMEEKYNLTSVLMAMGITDVFSSSANLSGISSAESLKISQAVHAAHAEINEAGR
EVVGSAEAGVDAASVSEEFRADHPFLFCIKHIATNAVLFFGRCVSP (SEQ ID NO: 71)

What we claim:

1. An isolated antibody, or an antigen-binding portion thereof, comprising a heavy chain variable region comprising a CDR1 region, a CDR2 region and a CDR3 region, wherein the CDR1 region, the CDR2 region and the CDR3 region comprise the amino acid sequences of:
   (1) SEQ ID NO: 1, 2, and 3, respectively; or
   (2) SEQ ID NO: 1, 2, and 4, respectively; and
Comprising a light chain variable region comprising a CDR1 region, a CDR2 region and a CDR3 region, wherein the CDR1 region, the CDR2 region and the CDR3 region comprise the amino acid sequences of SEQ ID NO: 5, 6, and 7, respectively; wherein the antibody or antigen-binding fragment thereof binds human PD-1.

2. The antibody, or the antigen-binding portion thereof, of claim 1, comprising a heavy chain variable region comprising an amino acid sequence having at least 80% identity to any one of SEQ ID NO: 8 to 16; and/or comprising a light chain variable region comprising an amino acid sequence having at least 80% identity to SEQ ID NO: 17.

3. The antibody, or the antigen-binding portion thereof, of claim 1, comprising a heavy chain and a light chain, wherein the heavy chain comprises an amino acid sequences having at least 80% identity to any one of SEQ ID NO: 21 to 38, and/or the light chain comprises an amino acid sequences having at least 80%, 85%, 90%, 95%, 98%, 99%, or 100% identity to SEQ ID NO: 39.

4. The antibody, or the antigen-binding portion thereof, of claim 1, which (a) binds to human PD-1; (b) binds to monkey PD-1; (c) does not bind to mouse PD-1; (d) does not cross react with CD28; (e) does not cross react with ICOS; (f) does not cross react with BTLA; (g) does not cross react with CTLA-4; (h) inhibits PD-1-PD-L1 interaction; (i) inhibits PD-1-PD-L2 interaction; (j) induces T cells to release IL-2; (k) induces T cells to release IFNγ; (l) does not induce ADCC on PD-1-expressing cells; and/or (m) does not induce CDC on PD-1-expressing cells.

5. The antibody, or the antigen-binding portion thereof, of claim 1, which is a human or chimeric antibody.

6. The antibody, or the antigen-binding portion thereof, of claim 1, which is an IgG1 or IgG4 isotype.

7. A pharmaceutical composition comprising the antibody, or antigen-binding portion thereof, of claim 1, and a pharmaceutically acceptable carrier.

8. The pharmaceutical composition of claim 7, further comprising an anti-tumor agent.

9. A method for treating a cancer disease in a subject, comprising administering to the subject a therapeutically effective amount of the pharmaceutical composition of claim 7.

10. The method of claim 9, wherein the cancer disease is selected from the group consisting of colon carcinoma, colorectal adenocarcinoma, lung cancer, lymphoma, mesothelioma, melanoma, and renal-cell cancer.

11. The method of claim 9, wherein a cytokine, costimulatory antibody, or at least one additional immunostimulatory antibody is further administered to the subject.

12. The method of claim 11, wherein the immunostimulatory antibody is an anti-LAG-3 antibody, an anti-PD-L1 antibody, an anti-TIM3 antibody or an anti-CTLA-4 antibody.

13. The method of claim 11, wherein, the cytokine is IL-2 or IL-21.

14. The method of claim 11, wherein the costimulatory antibody is an anti-CD137 or an anti-GITR antibody.

15. The antibody, or the antigen-binding portion thereof, of claim 1, which is a bispecific antibody.

16. The antibody, or the antigen-binding portion thereof, of claim 1, wherein the antibody is an scFv or wherein the antigen-binding portion is selected from a Fab fragment, an Fv fragment, and a F(ab')₂ fragment.

17. The antibody, or the antigen-binding portion thereof, of claim 1, which is a monoclonal antibody.

18. A nucleic acid molecule encoding the antibody or the antigen-binding portion thereof of claim 1.

19. An expression vector comprising the nucleic acid molecule of claim 18.

20. A host cell comprising the expression vector of claim 19.

21. A method for treating a cancer disease in a subject, comprising administering to the subject a therapeutically effective amount of the antibody, or antigen-binding portion thereof, of claim 1.

22. The antibody, or the antigen-binding portion thereof, of claim 1, wherein the CDR1 region, the CDR2 region and the CDR3 region in the heavy chain variable region consists of the amino acid sequences of:
   (1) SEQ ID NO: 1, 2, and 3, respectively; or
   (2) SEQ ID NO: 1, 2, and 4, respectively; and
the CDR1 region, the CDR2 region and the CDR3 region in the light chain variable region consists of the amino acid sequences of SEQ ID NO: 5, 6 and 7, respectively.

23. The antibody, or the antigen-binding portion thereof, of claim 2, wherein the heavy chain variable region comprises an amino acid sequence selected from any one of SEQ ID NO: 8-16; and/or comprises a light chain variable region comprising the amino acid sequence of SEQ ID NO: 17.

24. The antibody, or the antigen-binding portion thereof, of claim 3, wherein the heavy chain comprises an amino acid sequence selected from any one of SEQ ID NO: 21 to 38, and/or the light chain comprises the amino acid sequence of SEQ ID NO: 39.

* * * * *